United States Patent
Kuriyama et al.

(10) Patent No.: US 10,761,079 B2
(45) Date of Patent: Sep. 1, 2020

(54) METHOD OF ESTIMATING OVERHEATING TEMPERATURE OF OIL-IMMERSED ELECTRIC APPLIANCE

(71) Applicant: Mitsubishi Electric Corporation, Chiyoda-ku, Tokyo (JP)

(72) Inventors: Ryota Kuriyama, Tokyo (JP); Fukutaro Kato, Tokyo (JP); Shiki Hayamizu, Tokyo (JP); Kota Mizuno, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 16/307,824

(22) PCT Filed: Jun. 15, 2016

(86) PCT No.: PCT/JP2016/067745
§ 371 (c)(1),
(2) Date: Dec. 6, 2018

(87) PCT Pub. No.: WO2017/216890
PCT Pub. Date: Dec. 21, 2017

(65) Prior Publication Data
US 2019/0257812 A1    Aug. 22, 2019

(51) Int. Cl.
*G01N 33/28* (2006.01)
*G01N 21/3504* (2014.01)
(Continued)

(52) U.S. Cl.
CPC ....... *G01N 33/2841* (2013.01); *G01K 11/003* (2013.01); *G01N 21/3504* (2013.01);
(Continued)

(58) Field of Classification Search
CPC .......... G01N 21/3504; G01N 33/2841; G01N 33/2888; H01F 27/105; H01F 27/12
See application file for complete search history.

(56) References Cited

U.S. PATENT DOCUMENTS 4,744,905 A * 5/1988 Atwood .................... B08B 3/08
                                                    134/12
9,599,653 B2 * 3/2017 Kim ...................... G01R 31/027
(Continued)

FOREIGN PATENT DOCUMENTS

JP      2013131511 A    7/2013
JP         5872127 B1    3/2016

OTHER PUBLICATIONS

International Search Report (with English Translation) and Written Opinion issued in corresponding International Patent Application No. PCT/JP2016/067745, dated Aug. 9, 2016, 8 pages.
(Continued)

*Primary Examiner* — Francis C Gray
(74) *Attorney, Agent, or Firm* — Buchanan Ingersoll & Rooney PC

(57) ABSTRACT

The present invention is directed to a method of estimating an overheating temperature of an oil-immersed electric appliance in which ester oil is used as insulating oil. The overheating temperature is estimated based on a first concentration ratio representing a concentration ratio between two types of gas components contained in the ester oil and a second concentration ratio representing a concentration ratio between other two types of gas components contained in the ester oil. The first concentration ratio and the second concentration ratio are selected from a concentration ratio between acetylene and ethane, a concentration ratio between acetylene and hydrogen, a concentration ratio between acetylene and methane, and a concentration ratio between acetylene and ethylene.

4 Claims, 26 Drawing Sheets

(51) Int. Cl.
- *H01F 27/10* (2006.01)
- *H01F 27/12* (2006.01)
- *G01K 11/00* (2006.01)

(52) U.S. Cl.
CPC ....... *G01N 33/2888* (2013.01); *H01F 27/105* (2013.01); *H01F 27/12* (2013.01)

(56) References Cited

U.S. PATENT DOCUMENTS

| | | | |
|---|---|---|---|
| 2007/0222546 A1* | 9/2007 | Bessede | C10M 111/02 336/58 |
| 2013/0204827 A1* | 8/2013 | Kawachi | G01N 33/2841 706/46 |
| 2014/0036954 A1* | 2/2014 | Maity | G01J 5/0014 374/121 |
| 2014/0165704 A1* | 6/2014 | Maity | G01N 33/2841 73/25.01 |
| 2015/0020572 A1* | 1/2015 | Kim | G01R 31/62 73/19.01 |
| 2017/0138922 A1* | 5/2017 | Potyrailo | G01M 13/021 |
| 2017/0199170 A1* | 7/2017 | Kuriyama | G01N 30/02 |
| 2018/0143176 A1 | 5/2018 | Kuriyama et al. | |

OTHER PUBLICATIONS

Unknown, "Aburairi Hen-atsuki no Hoshu Kanri," Electric Technology Research Association, Denki Kyodo Kenkyu, vol. 54, No. 5 (1), Feb. 1999.

Wang, et al., "Gas Generation in Natural Ester and Mineral Oil Under Partial Discharge and Sparking Faults," IEEE Electrical Insulation Magazine, vol. 29, No. 5, Sep./Oct. 2013, pp. 62-70.

* cited by examiner

I (ACETYLENE/ETHANE)

$y = 0.0000000801\, e^{0.0163616701\, x}$
$R^2 = 0.9994329606$

J (ACETYLENE/ETHYLENE)

$y = 0.000000205\, e^{0.013286502\, x}$
$R^2 = 0.998073031$

A (ETHYLENE/ETHANE)

B (ETHYLENE/METHANE)

METHOD OF ESTIMATING OVERHEATING TEMPERATURE OF OIL-IMMERSED ELECTRIC APPLIANCE

TECHNICAL FIELD

The present invention relates to a method of estimating an overheating temperature of an oil-immersed electric appliance in which ester oil is used as insulating oil.

BACKGROUND ART

A method of diagnosing a fault such as overheat abnormality of an oil-immersed electric appliance such as a transformer without turning off the appliance with a type or a concentration of a gas component in insulating oil or a concentration ratio between a plurality of gas components being defined as an indicator has been known (for example, NPL 1 (Z. Wang, X. Wang, X. Yi and S. Li, "Gas Generation in Natural Ester and Mineral Oil Under Partial Discharge and Sparking Faults," IEEE Electrical Insulation Magazine, Vol. 29, No. 5, pp. 62-70, 2013) and NPL 2 (Denki Kyodo Kenkyu, Vol. 54, No. 5 (1), Aburairi Hen-atsuki no Hoshu Kanri, Electric Technology Research Association, February 1999)).

Many works associated with such a fault diagnosis method for an oil-immersed transformer in which mineral oil is employed as insulating oil through analysis of gas in oil have been built up and guidelines for diagnosis of a fault have also been proposed domestically and abroad.

For example, in an oil-immersed electric appliance (such as a transformer) to be mounted on a vehicle (such as a rail vehicle), with safety being focused on, non-mineral oil based insulating oil (such as silicone oil) higher in flash point and higher in safety than mineral oil is sometimes employed. In recent years, ester oil which is excellent not only in safety but also in biodegradability and low in environmental loads has increasingly been applied (for example, PTL 1 (Japanese Patent Laying-Open No. 2013-131511)).

Non-mineral oil based insulating oil such as silicone oil or ester oil, however, is different in composition from mineral oil, and therefore it is different from mineral oil in type and ratio of concentration of gas components generated at the time of occurrence of such a fault as discharging and overheating.

PTL 2 (Japanese Patent No. 5872127) discloses a method of diagnosing a fault (estimating an overheating temperature) based on a concentration ratio between gas components in silicone oil in an oil-immersed electric appliance in which silicone oil is employed as insulating oil.

CITATION LIST

Patent Literature

PTL 1: Japanese Patent Laying-Open No. 2013-131511
PTL 2: Japanese Patent No. 5872127

Non Patent Literature

NPL 1: Z. Wang, X. Wang, X. Yi and S. Li, "Gas Generation in Natural Ester and Mineral Oil Under Partial Discharge and Sparking Faults," IEEE Electrical Insulation Magazine, Vol. 29, No. 5, pp. 62-70, 2013

NPL 2: Denki Kyodo Kenkyu, Vol. 54, No. 5 (1), Aburairi Hen-atsuki no Hoshu Kanri, Electric Technology Research Association, February 1999

SUMMARY OF INVENTION

Technical Problem

A method of estimating an overheating temperature of an oil-immersed electric appliance in which ester oil is used, however, has not been established.

Since ester oil is different in composition from mineral oil and silicone oil, ester oil is different from mineral oil and silicone oil in type and concentration of gas components generated at the time of occurrence of such a fault as discharge abnormality and overheat abnormality and in concentration ratio between a plurality of gas components. Therefore, it is not appropriate to apply as it is a method of estimating an overheating temperature of an oil-immersed electric appliance in which mineral oil and silicone oil are used to estimation of an overheating temperature of an oil-immersed electric appliance in which ester oil is used.

The present invention was made in view of the problems above, and an object thereof is to highly accurately estimate an overheating temperature of an oil-immersed electric appliance in which ester oil is used as insulating oil, with a gas component in the ester oil being defined as an indicator.

Solution to Problem

The present invention is directed to a method of estimating an overheating temperature of an oil-immersed electric appliance in which ester oil is used as insulating oil. An overheating temperature is estimated based on a first concentration ratio representing a concentration ratio between two types of gas components contained in the ester oil and a second concentration ratio representing a concentration ratio between other two types of gas components contained in the ester oil. The first concentration ratio and the second concentration ratio are selected from a concentration ratio between acetylene and ethane, a concentration ratio between acetylene and hydrogen, a concentration ratio between acetylene and methane, and a concentration ratio between acetylene and ethylene.

Advantageous Effects of Invention

According to the present invention, an overheating temperature of an oil-immersed electric appliance in which ester oil is used as insulating oil can highly accurately be estimated with a gas component in the ester oil being defined as an indicator.

DESCRIPTION OF EMBODIMENTS

Figure 1:
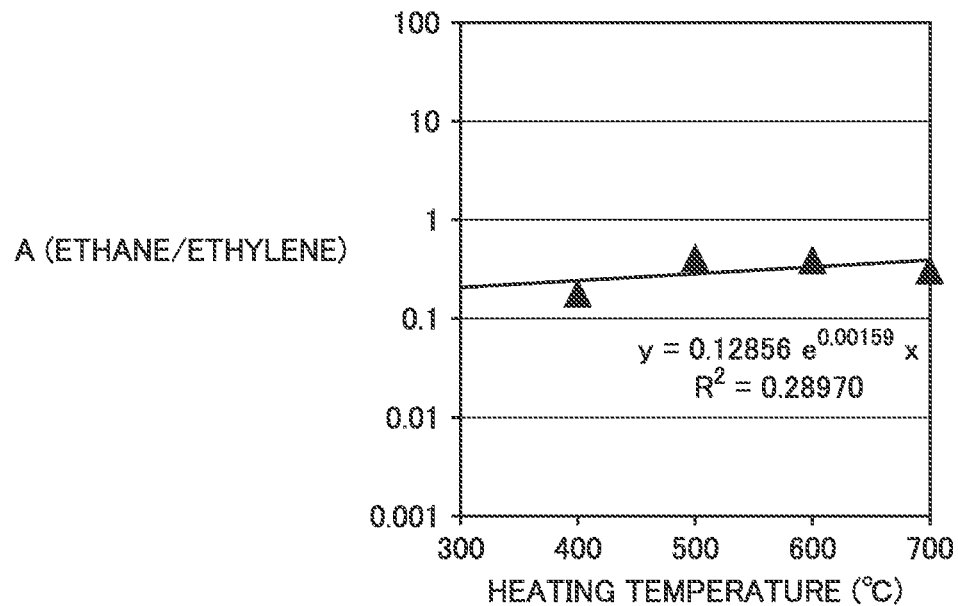
FIG. 1 is a graph showing relation between a gas component concentration ratio and a heating temperature (not higher than 700° C.) shown in Table 3, of synthetic ester oil.
Figure 2:
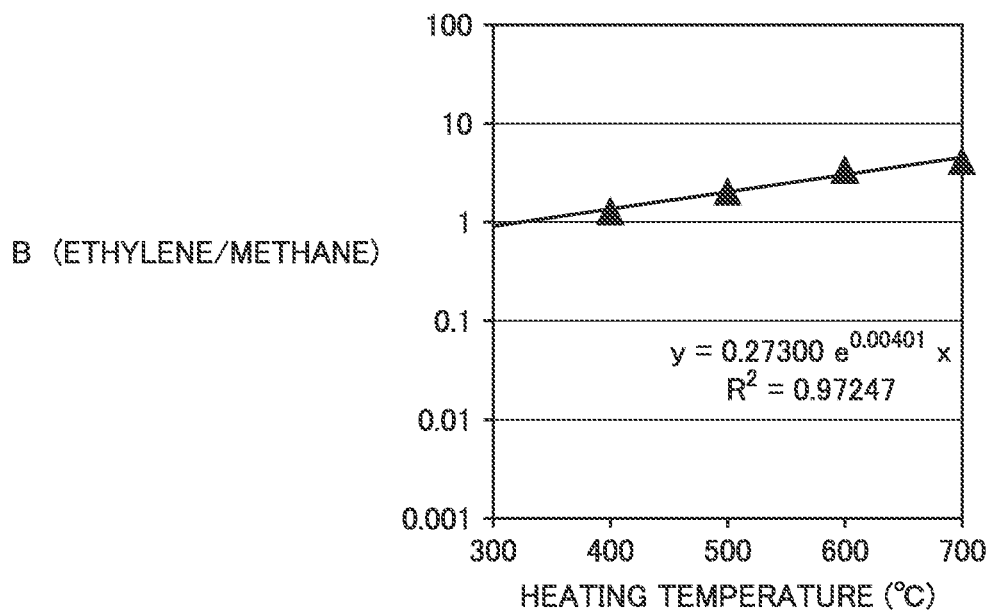
FIG. 2 is a graph showing relation between a gas component concentration ratio and a heating temperature (not higher than 700° C.) shown in Table 3, of synthetic ester oil.
Figure 3:
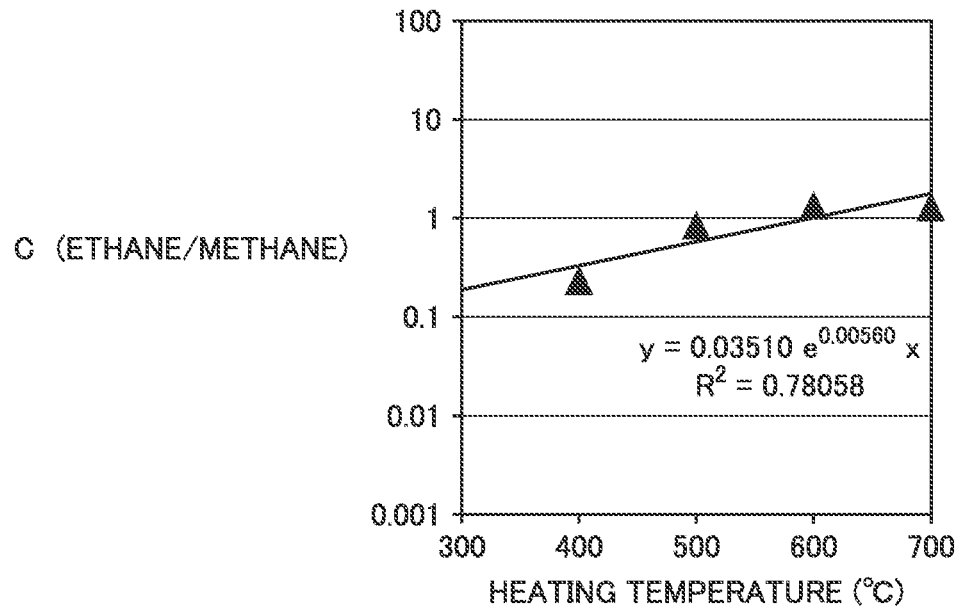
FIG. 3 is a graph showing relation between a gas component concentration ratio and a heating temperature (not higher than 700° C.) shown in Table 3, of synthetic ester oil.
Figure 4:
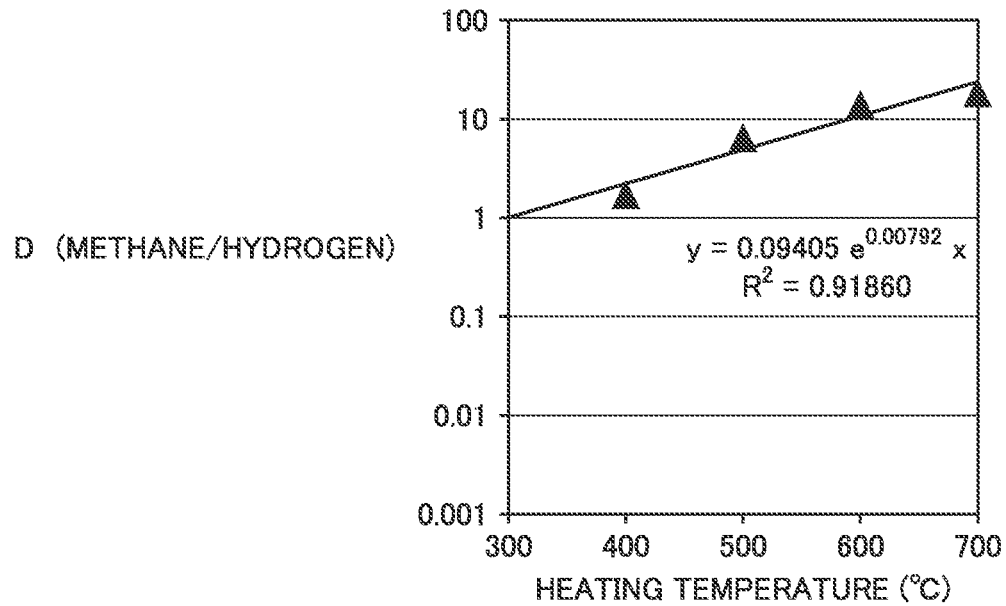
FIG. 4 is a graph showing relation between a gas component concentration ratio and a heating temperature (not higher than 700° C.) shown in Table 3, of synthetic ester oil.
Figure 5:
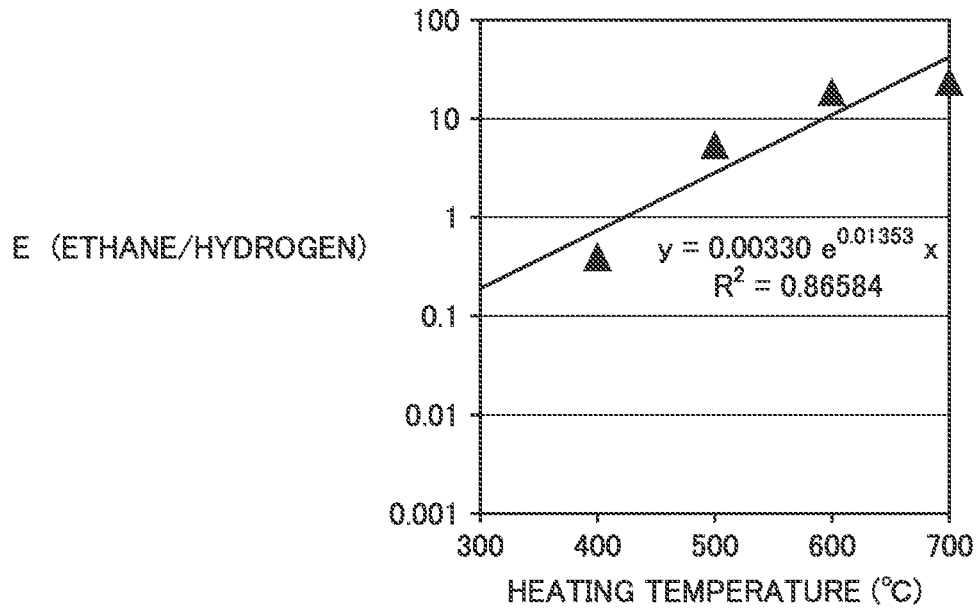
FIG. 5 is a graph showing relation between a gas component concentration ratio and a heating temperature (not higher than 700° C.) shown in Table 3, of synthetic ester oil.
Figure 6:
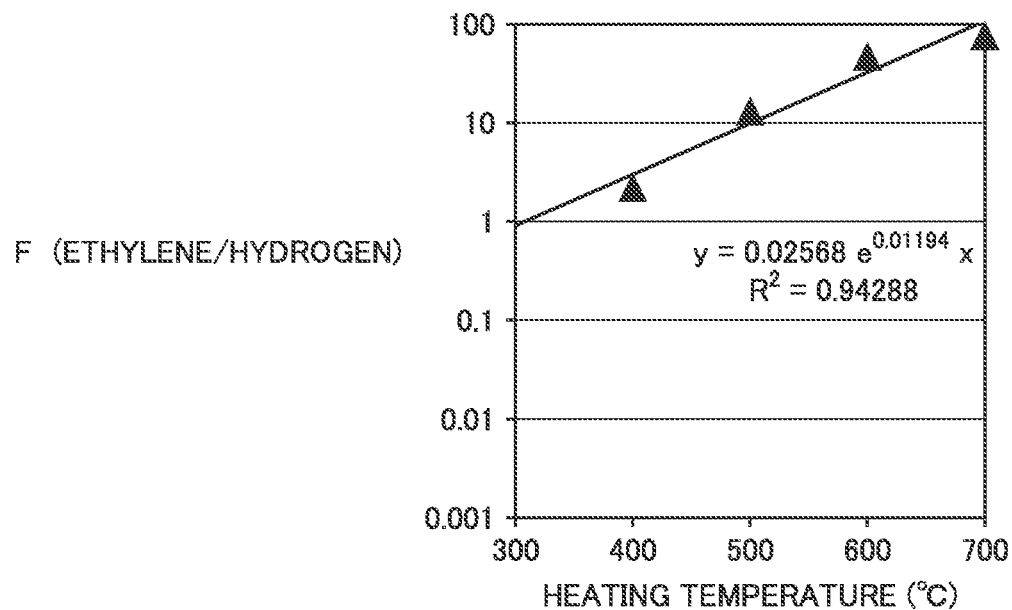
FIG. 6 is a graph showing relation between a gas component concentration ratio and a heating temperature (not higher than 700° C.) shown in Table 3, of synthetic ester oil.
Figure 7:
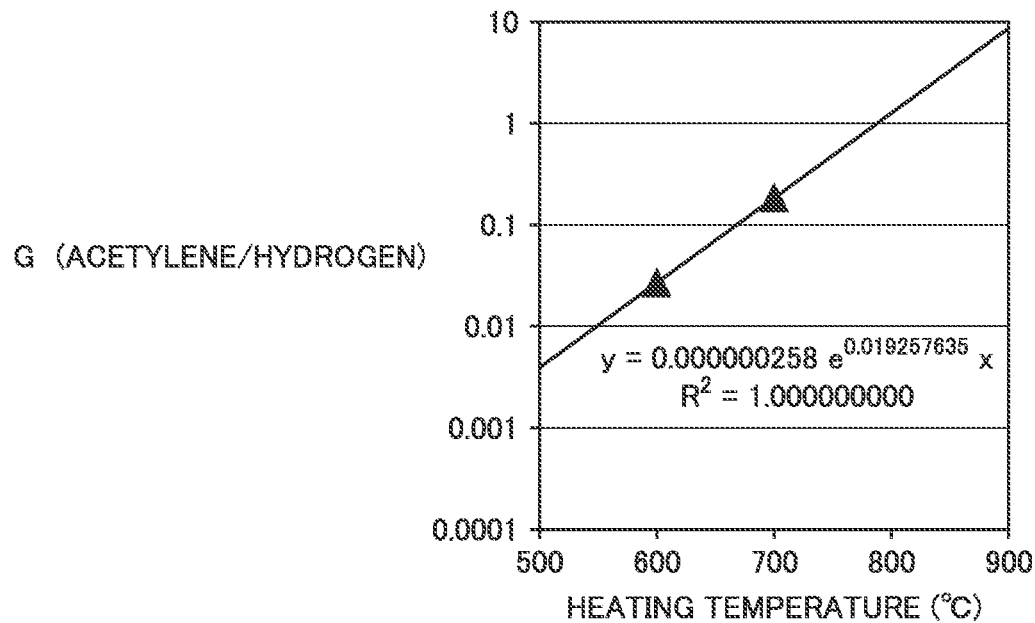
FIG. 7 is a graph showing relation between a gas component concentration ratio and a heating temperature (not higher than 700° C.) shown in Table 3, of synthetic ester oil.
Figure 8:
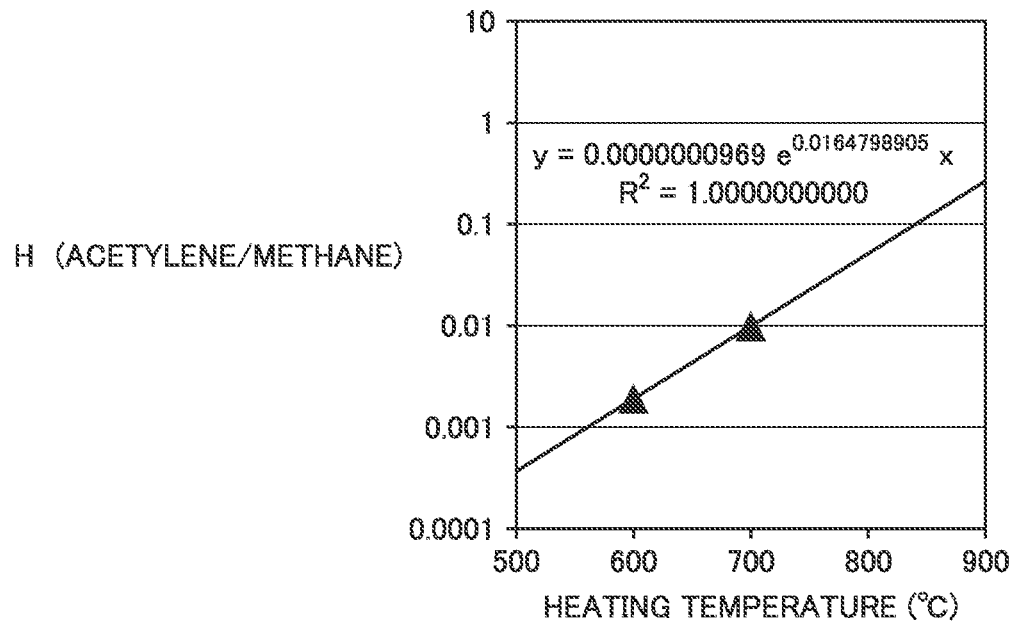
FIG. 8 is a graph showing relation between a gas component concentration ratio and a heating temperature (not higher than 700° C.) shown in Table 3, of synthetic ester oil.
Figure 9:
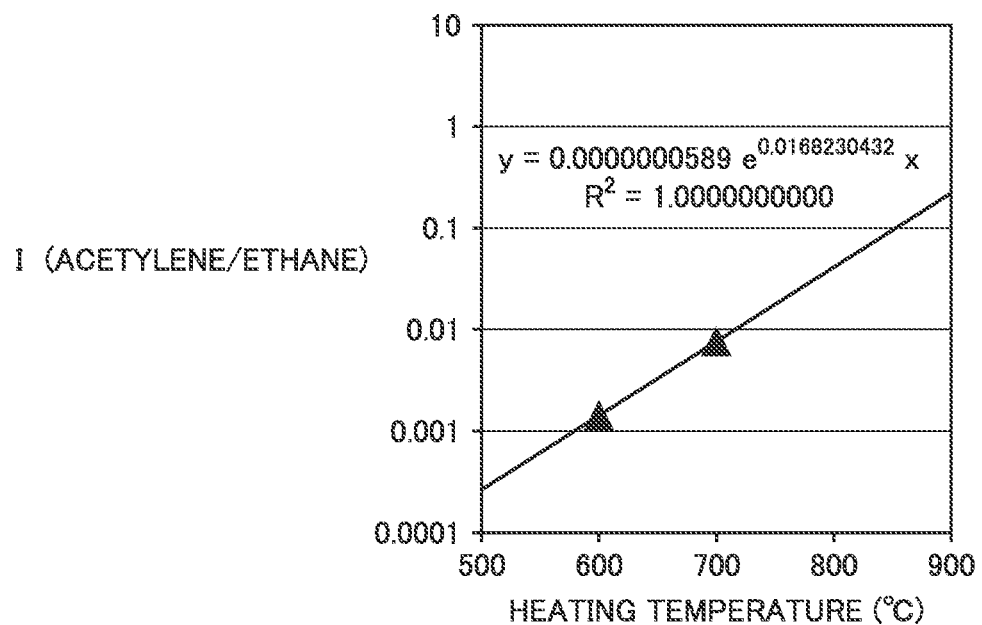
FIG. 9 is a graph showing relation between a gas component concentration ratio and a heating temperature (not higher than 700° C.) shown in Table 3, of synthetic ester oil.
Figure 10:
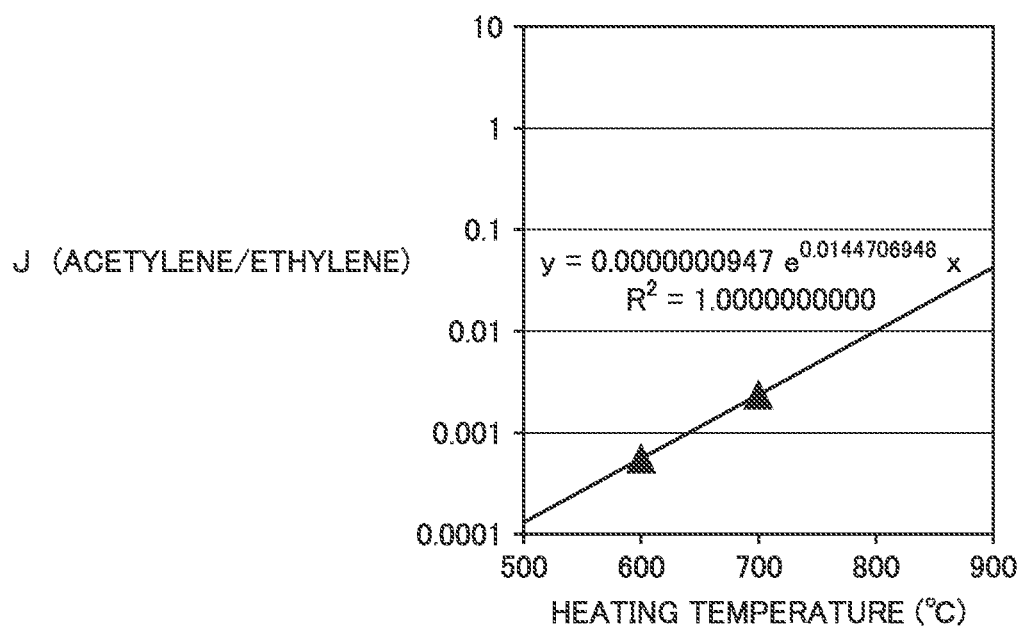
FIG. 10 is a graph showing relation between a gas component concentration ratio and a heating temperature (not higher than 700° C.) shown in Table 3, of synthetic ester oil.
Figure 11:
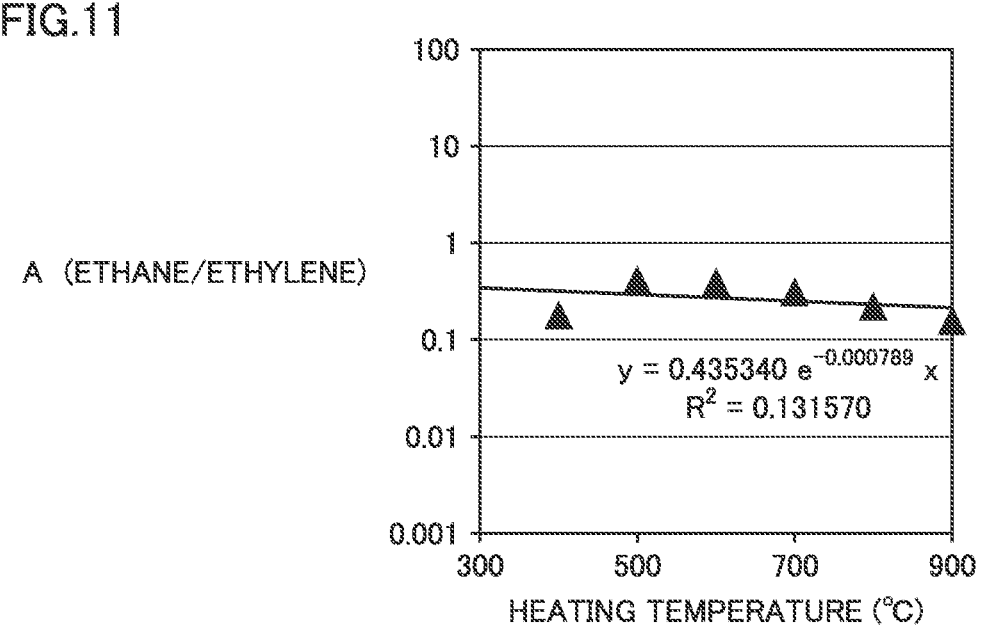
FIG. 11 is a graph showing relation between a gas component concentration ratio and a heating temperature (not higher than 900° C.) shown in Table 3, of synthetic ester oil.
Figure 12:
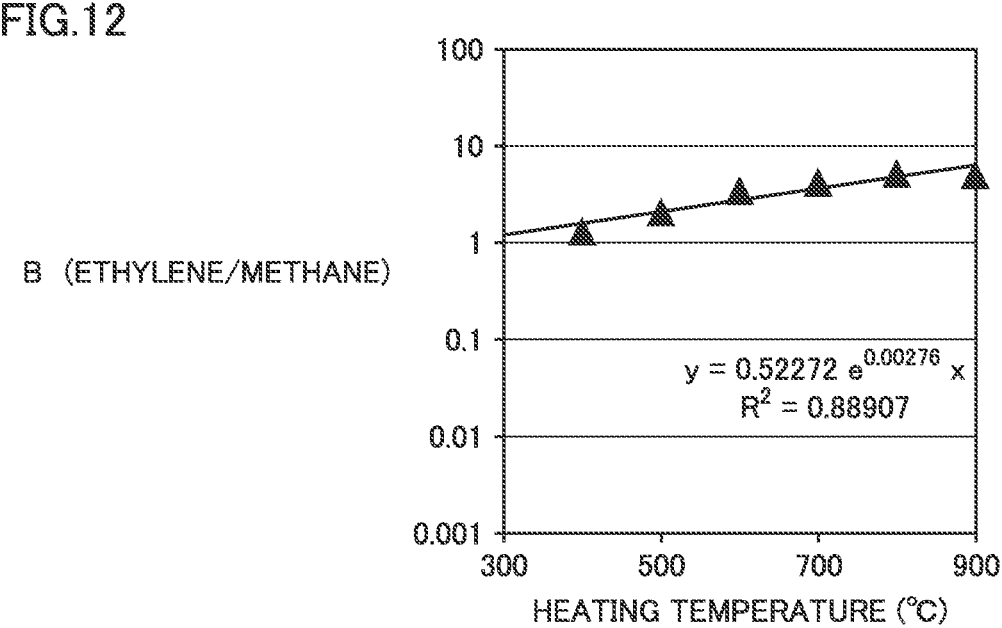
FIG. 12 is a graph showing relation between a gas component concentration ratio and a heating temperature (not higher than 900° C.) shown in Table 3, of synthetic ester oil.
Figure 13:
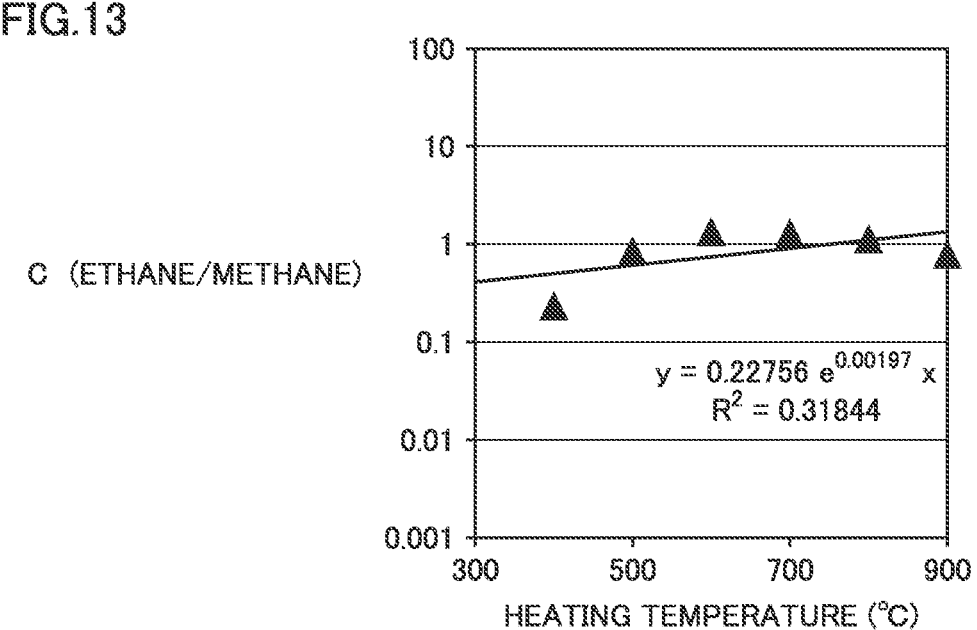
FIG. 13 is a graph showing relation between a gas component concentration ratio and a heating temperature (not higher than 900° C.) shown in Table 3, of synthetic ester oil.
Figure 14:
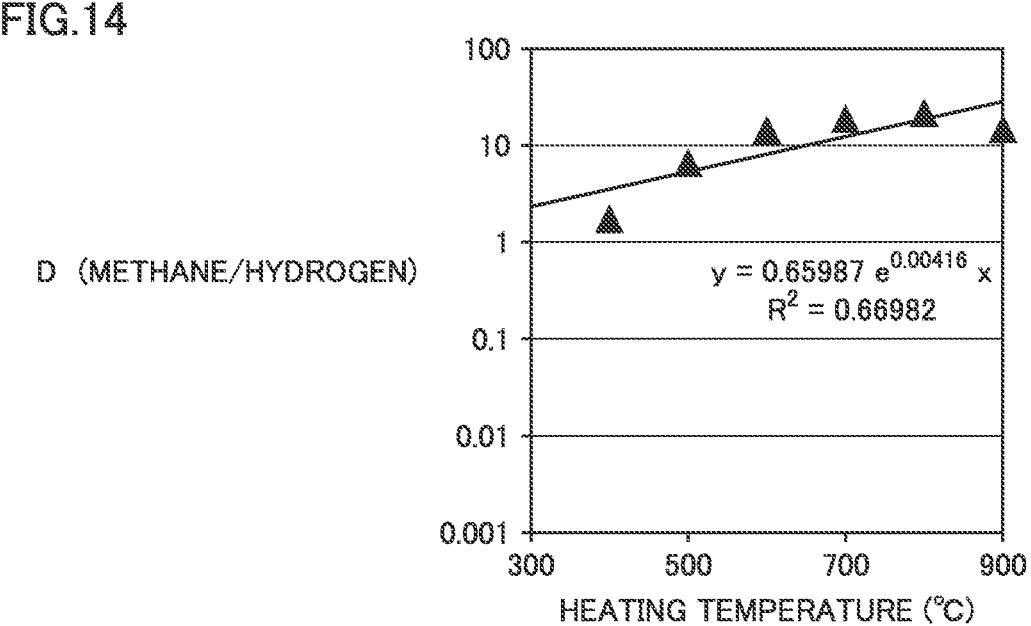
FIG. 14 is a graph showing relation between a gas component concentration ratio and a heating temperature (not higher than 900° C.) shown in Table 3, of synthetic ester oil.
Figure 15:
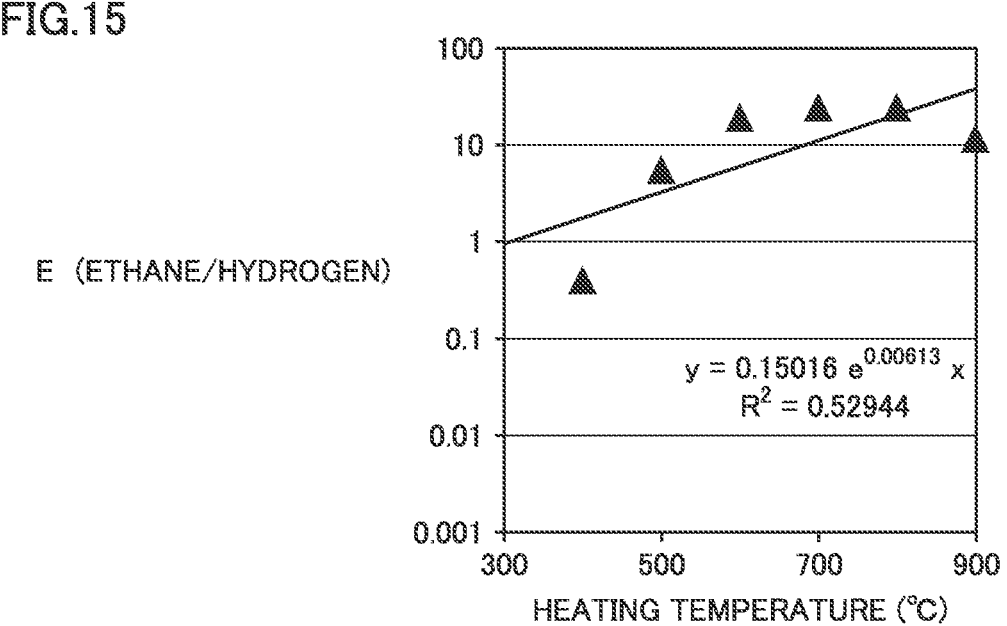
FIG. 15 is a graph showing relation between a gas component concentration ratio and a heating temperature (not higher than 900° C.) shown in Table 3, of synthetic ester oil.
Figure 16:
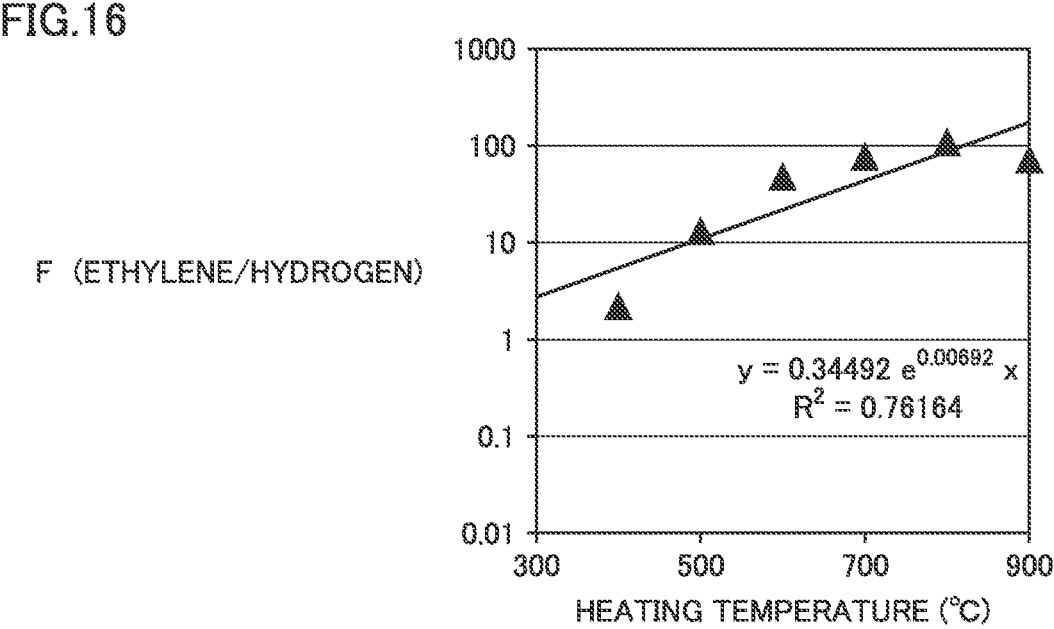
FIG. 16 is a graph showing relation between a gas component concentration ratio and a heating temperature (not higher than 900° C.) shown in Table 3, of synthetic ester oil.
Figure 17:
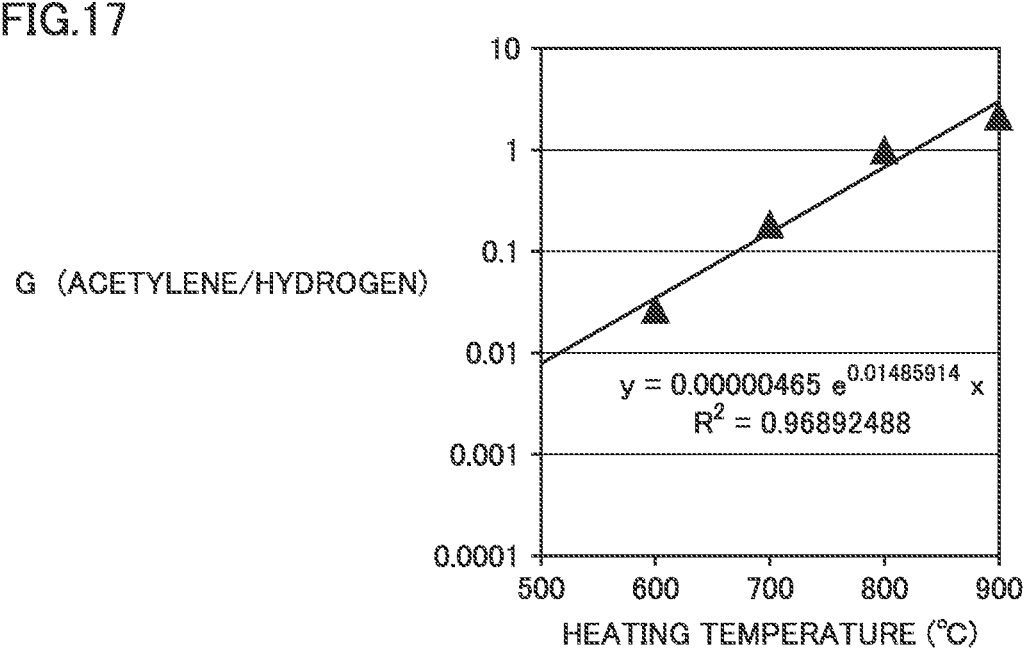
FIG. 17 is a graph showing relation between a gas component concentration ratio and a heating temperature (not higher than 900° C.) shown in Table 3, of synthetic ester oil.
Figure 18:
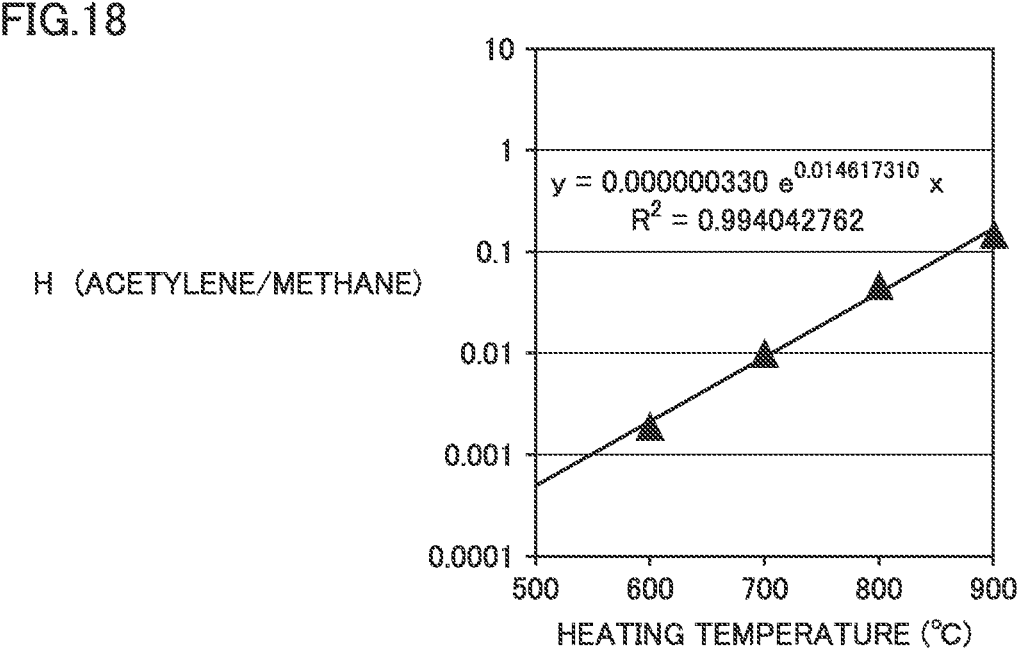
FIG. 18 is a graph showing relation between a gas component concentration ratio and a heating temperature (not higher than 900° C.) shown in Table 3, of synthetic ester oil.
Figure 19:
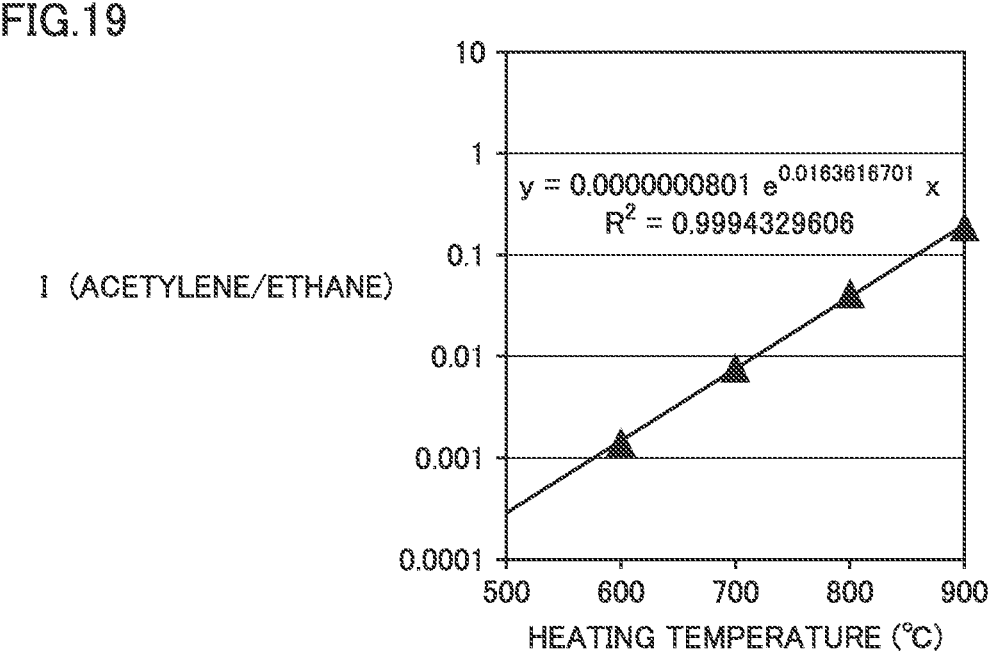
FIG. 19 is a graph showing relation between a gas component concentration ratio and a heating temperature (not higher than 900° C.) shown in Table 3, of synthetic ester oil.
Figure 20:
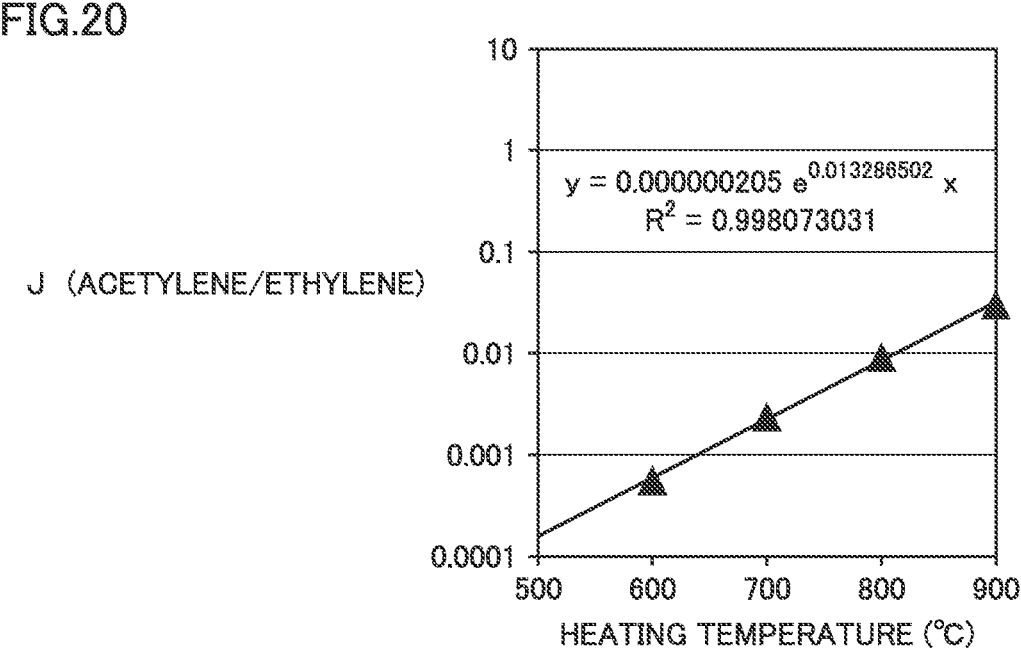
FIG. 20 is a graph showing relation between a gas component concentration ratio and a heating temperature (not higher than 900° C.) shown in Table 3, of synthetic ester oil.
Figure 21:
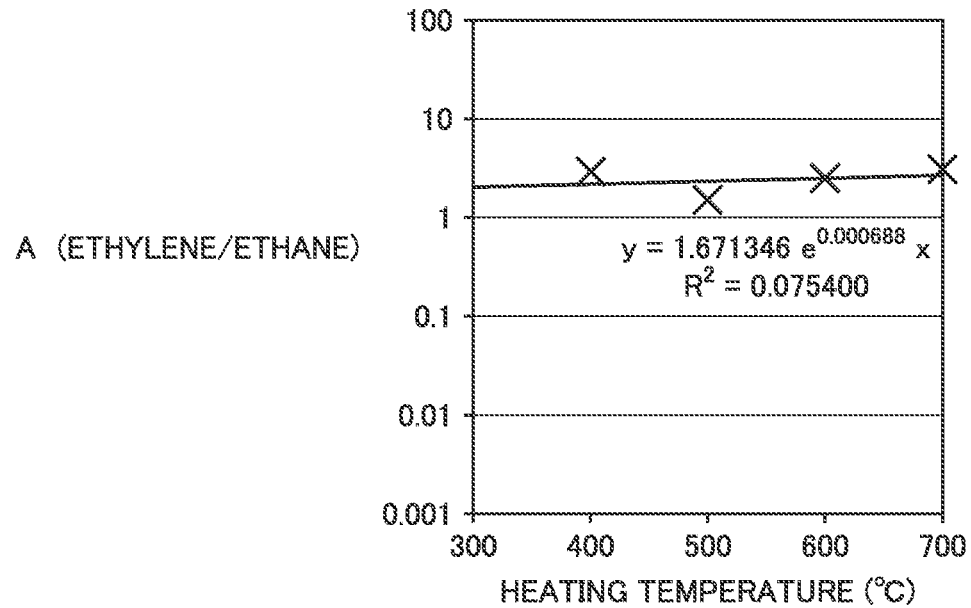
FIG. 21 is a graph showing relation between a gas component concentration ratio and a heating temperature (not higher than 700° C.) shown in Table 3, of natural ester oil.
Figure 22:
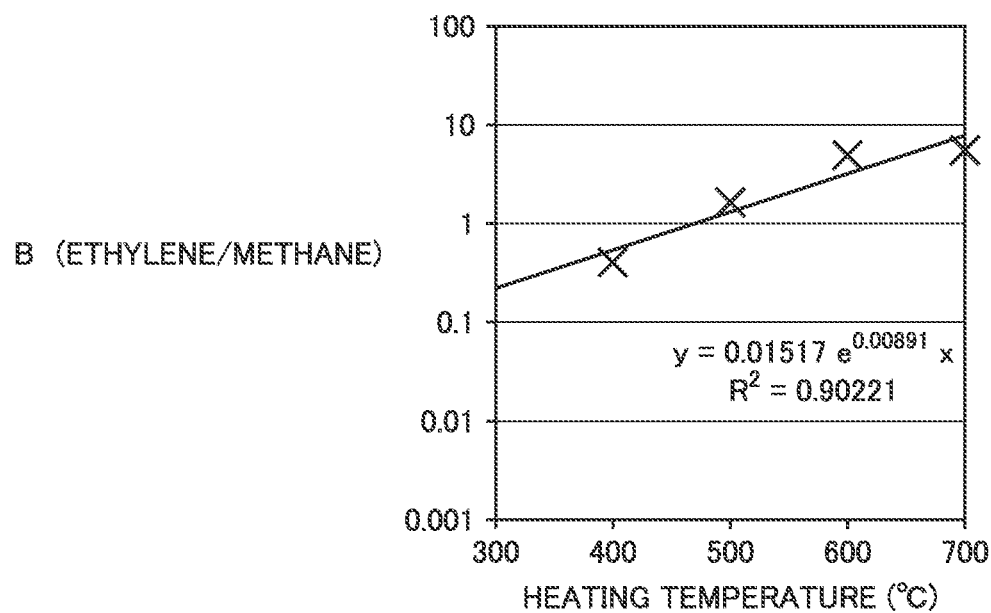
FIG. 22 is a graph showing relation between a gas component concentration ratio and a heating temperature (not higher than 700° C.) shown in Table 3, of natural ester oil.
Figure 23:
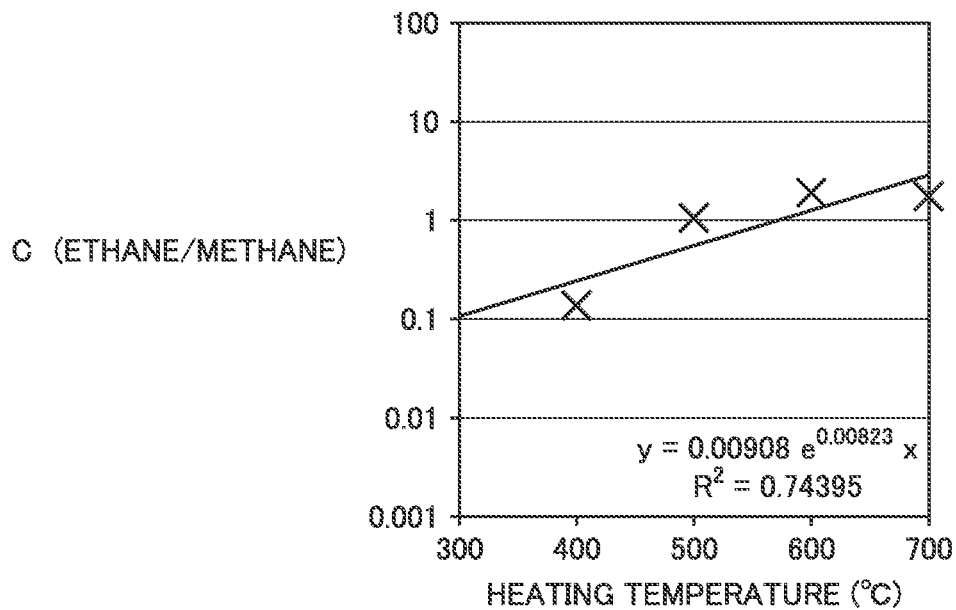
FIG. 23 is a graph showing relation between a gas component concentration ratio and a heating temperature (not higher than 700° C.) shown in Table 3, of natural ester oil.
Figure 24:
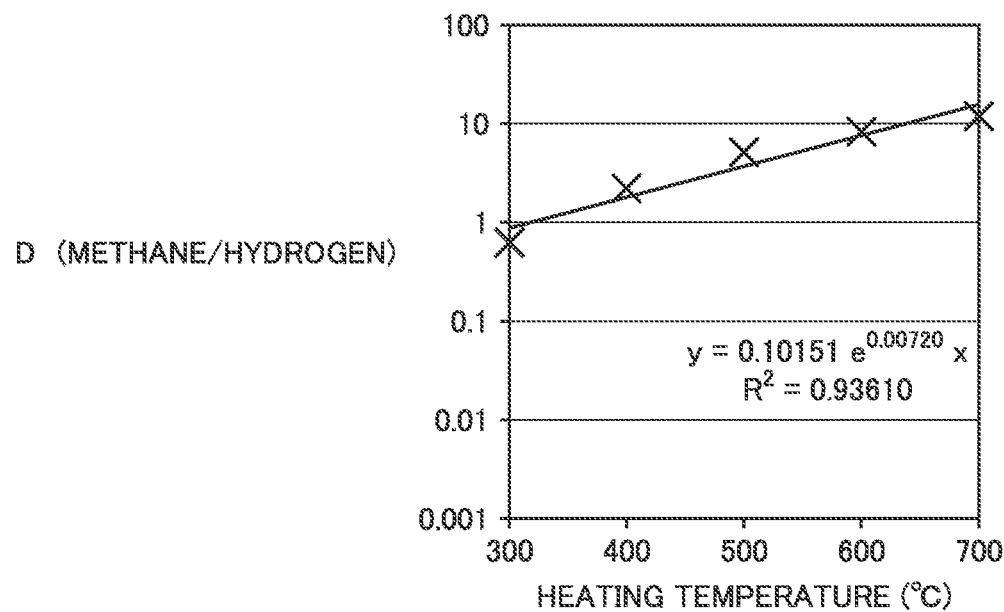
FIG. 24 is a graph showing relation between a gas component concentration ratio and a heating temperature (not higher than 700° C.) shown in Table 3, of natural ester oil.
Figure 25:
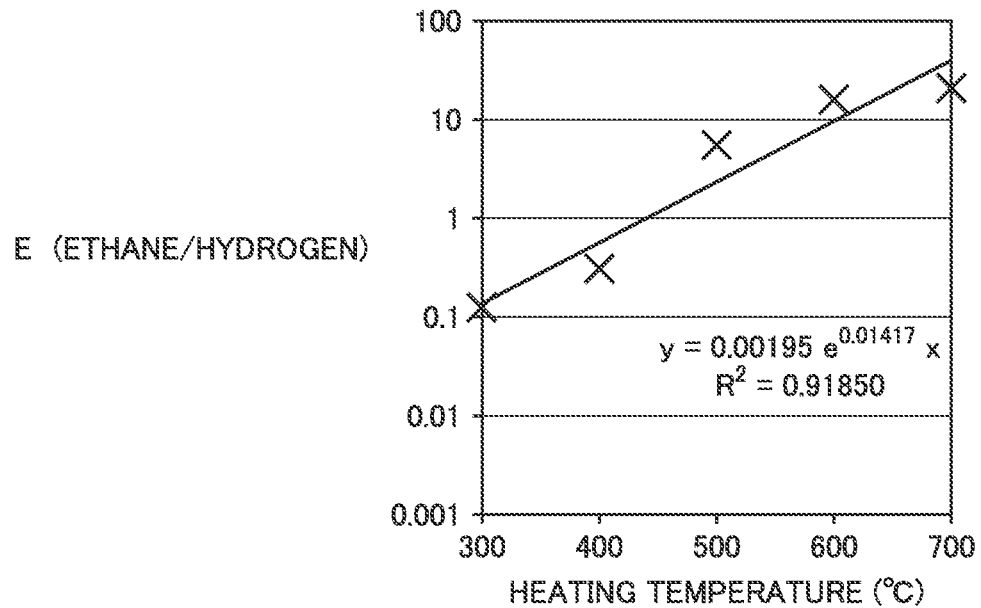
FIG. 25 is a graph showing relation between a gas component concentration ratio and a heating temperature (not higher than 700° C.) shown in Table 3, of natural ester oil.
Figure 26:
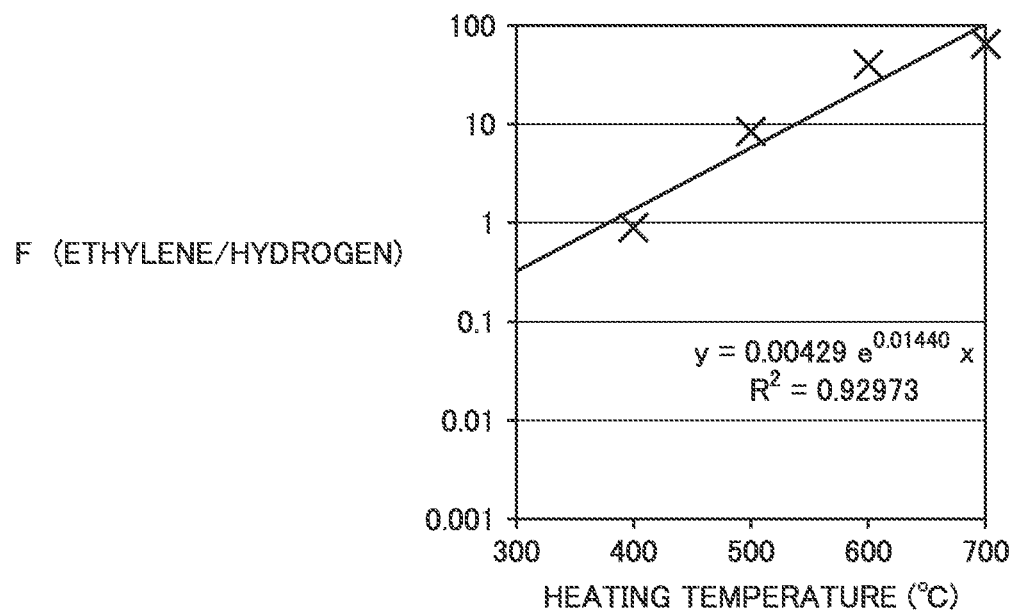
FIG. 26 is a graph showing relation between a gas component concentration ratio and a heating temperature (not higher than 700° C.) shown in Table 3, of natural ester oil.
Figure 27:
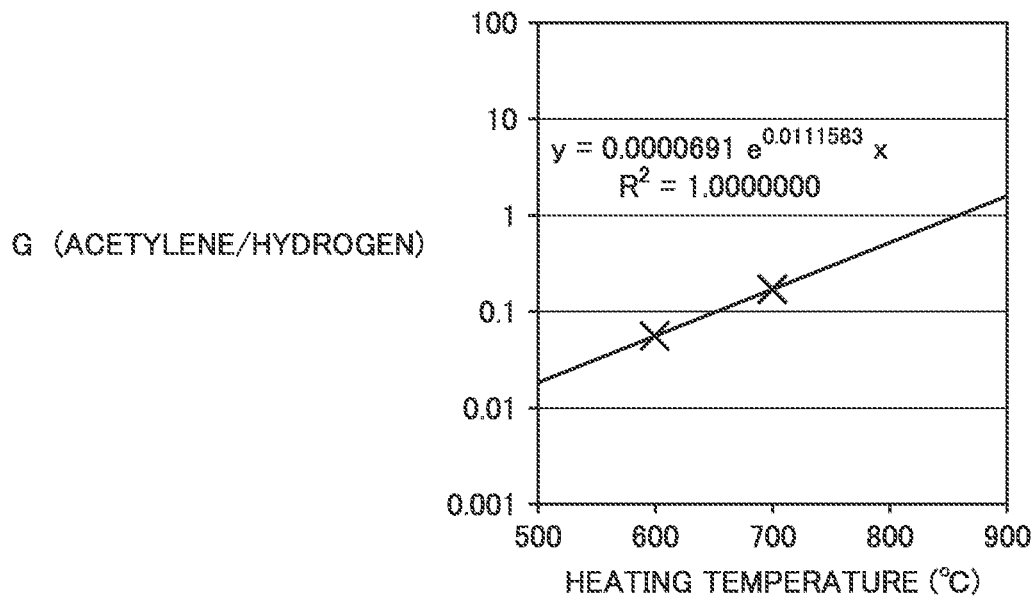
FIG. 27 is a graph showing relation between a gas component concentration ratio and a heating temperature (not higher than 700° C.) shown in Table 3, of natural ester oil.
Figure 28:
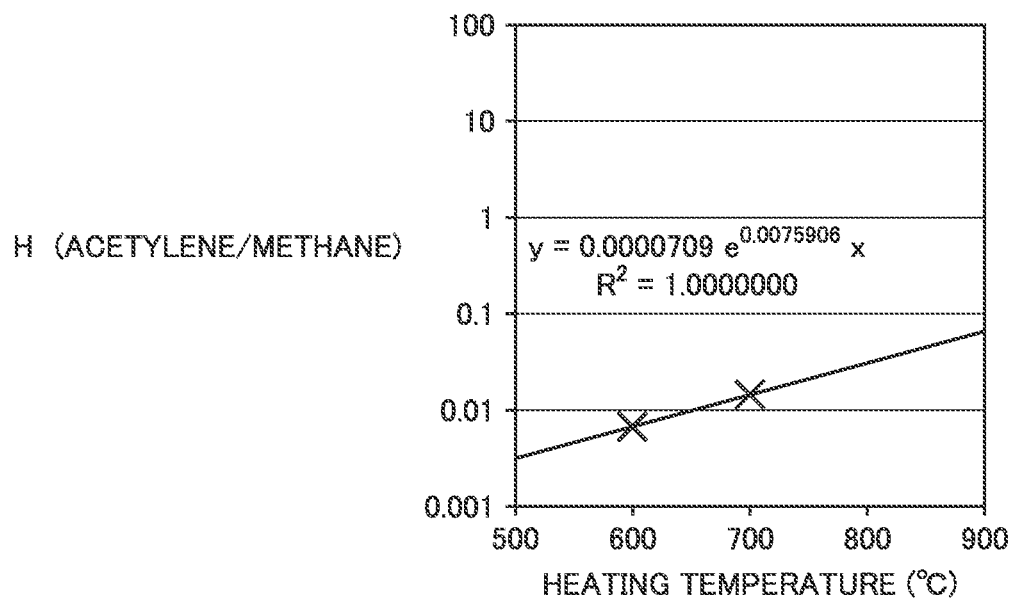
FIG. 28 is a graph showing relation between a gas component concentration ratio and a heating temperature (not higher than 700° C.) shown in Table 3, of natural ester oil.
Figure 29:
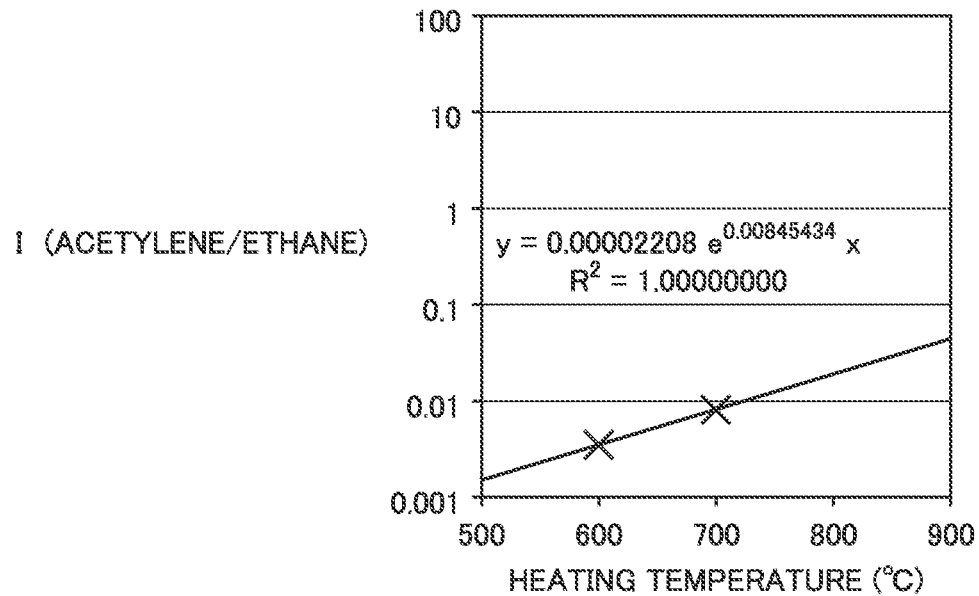
FIG. 29 is a graph showing relation between a gas component concentration ratio and a heating temperature (not higher than 700° C.) shown in Table 3, of natural ester oil.
Figure 30:
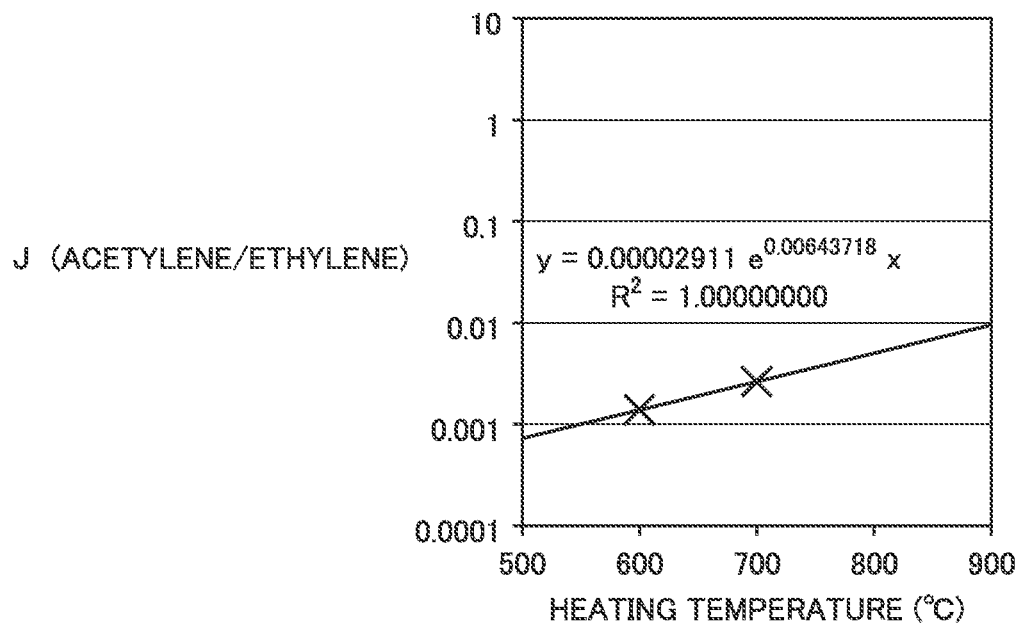
FIG. 30 is a graph showing relation between a gas component concentration ratio and a heating temperature (not higher than 700° C.) shown in Table 3, of natural ester oil.
Figure 31:
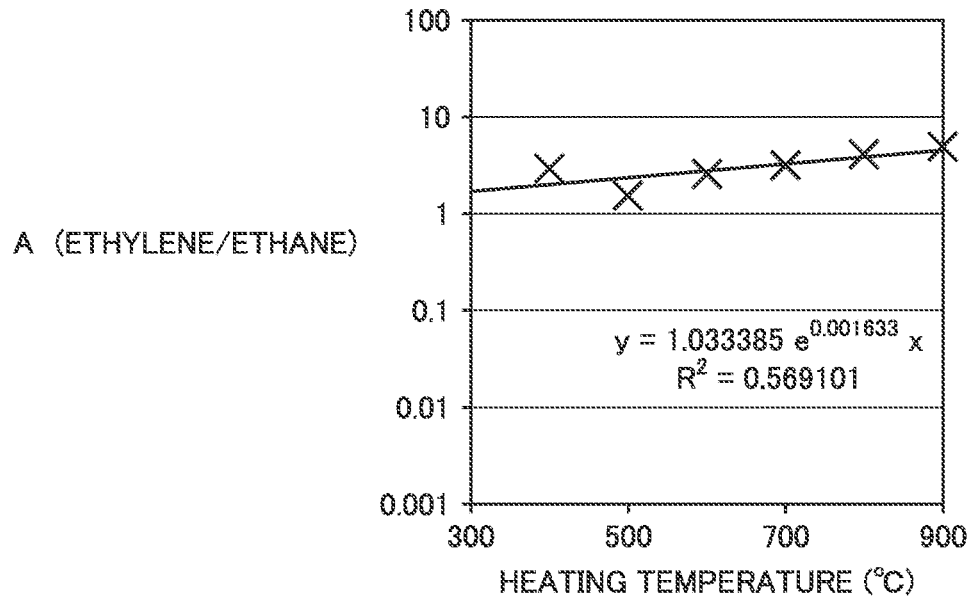
FIG. 31 is a graph showing relation between a gas component concentration ratio and a heating temperature (not higher than 900° C.) shown in Table 3, of natural ester oil.
Figure 32:
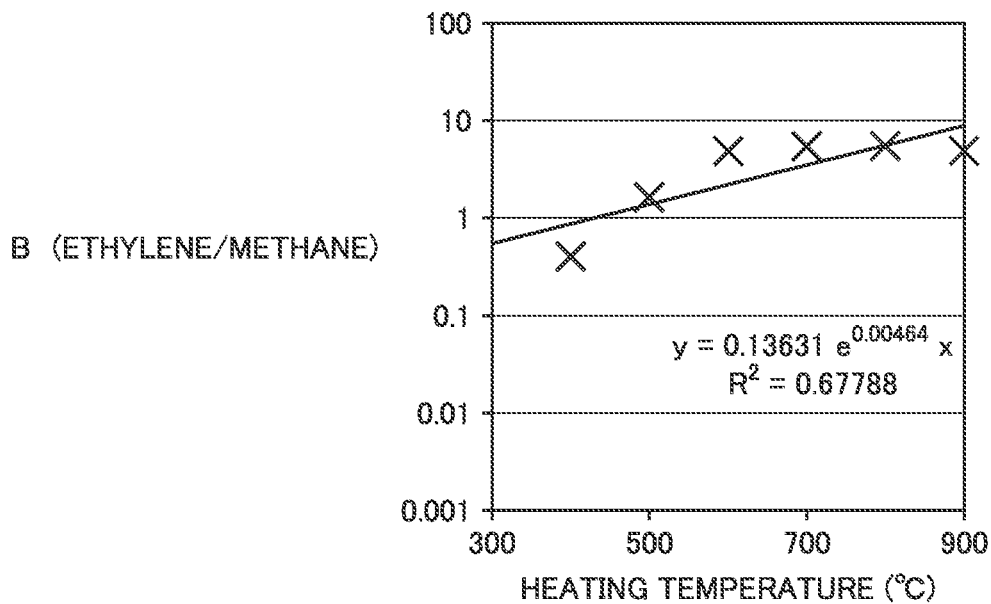
FIG. 32 is a graph showing relation between a gas component concentration ratio and a heating temperature (not higher than 900° C.) shown in Table 3, of natural ester oil.
Figure 33:
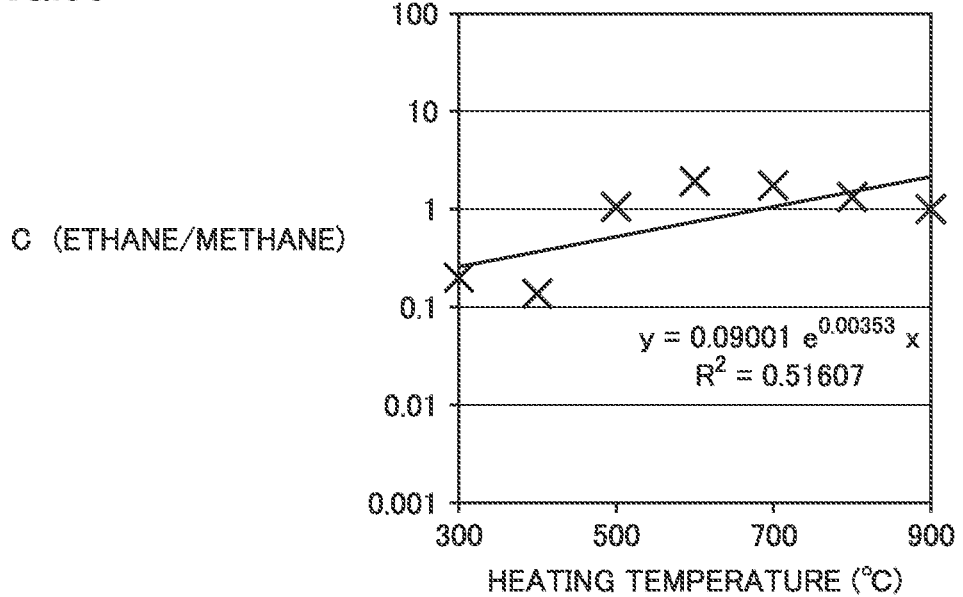
FIG. 33 is a graph showing relation between a gas component concentration ratio and a heating temperature (not higher than 900° C.) shown in Table 3, of natural ester oil.
Figure 34:
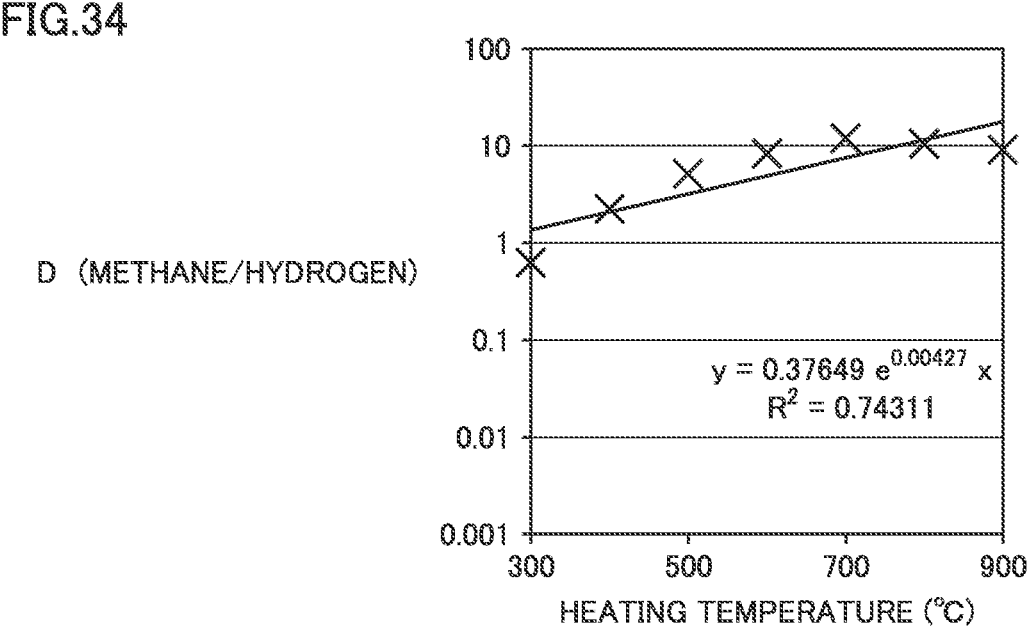
FIG. 34 is a graph showing relation between a gas component concentration ratio and a heating temperature (not higher than 900° C.) shown in Table 3, of natural ester oil.
Figure 35:
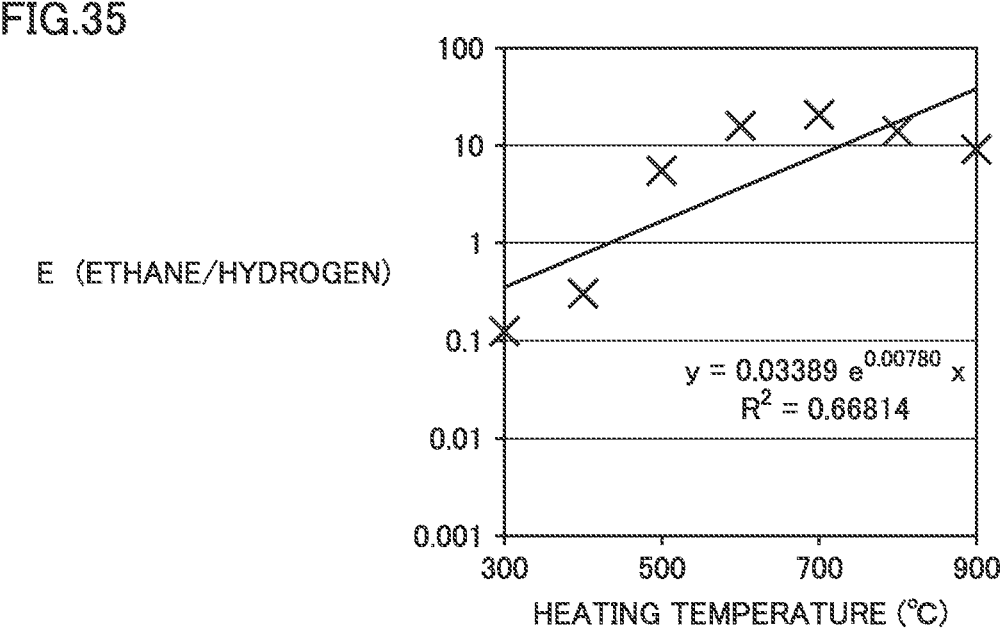
FIG. 35 is a graph showing relation between a gas component concentration ratio and a heating temperature (not higher than 900° C.) shown in Table 3, of natural ester oil.
Figure 36:
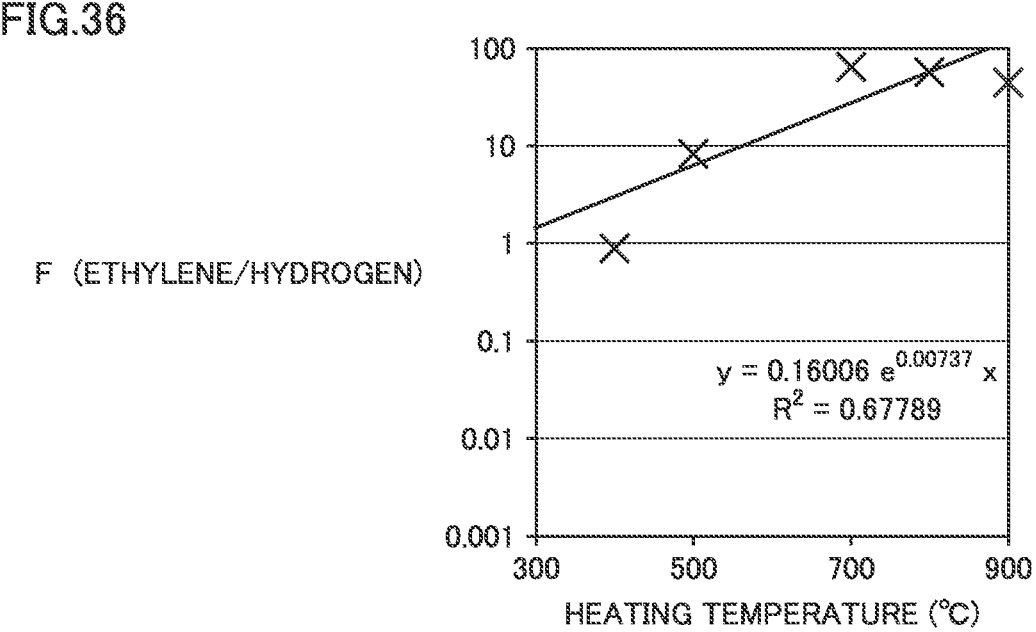
FIG. 36 is a graph showing relation between a gas component concentration ratio and a heating temperature (not higher than 900° C.) shown in Table 3, of natural ester oil.
Figure 37:
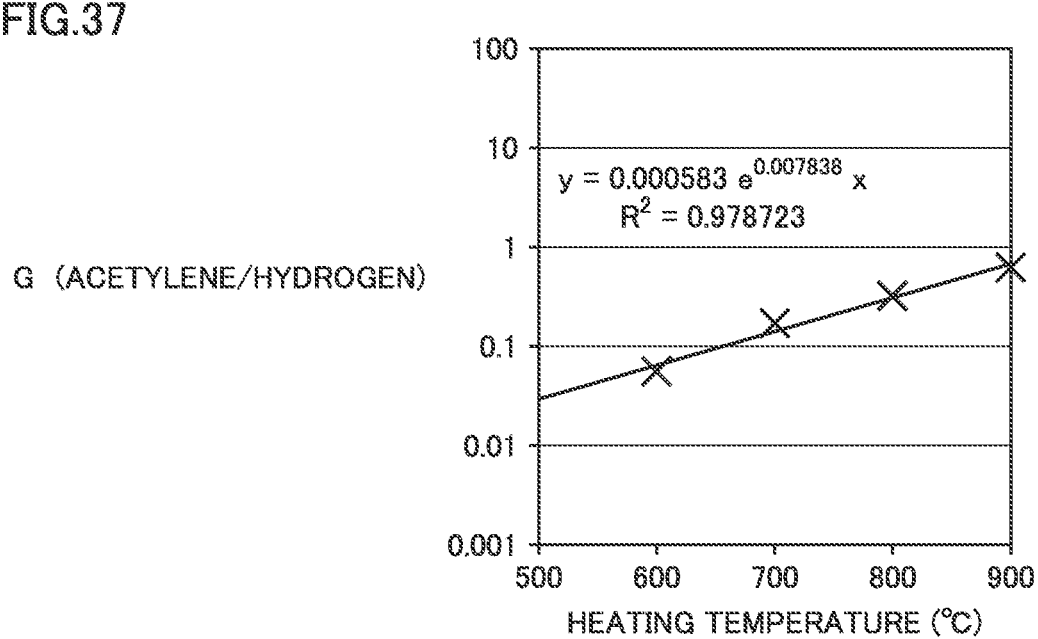
FIG. 37 is a graph showing relation between a gas component concentration ratio and a heating temperature (not higher than 900° C.) shown in Table 3, of natural ester oil.
Figure 38:
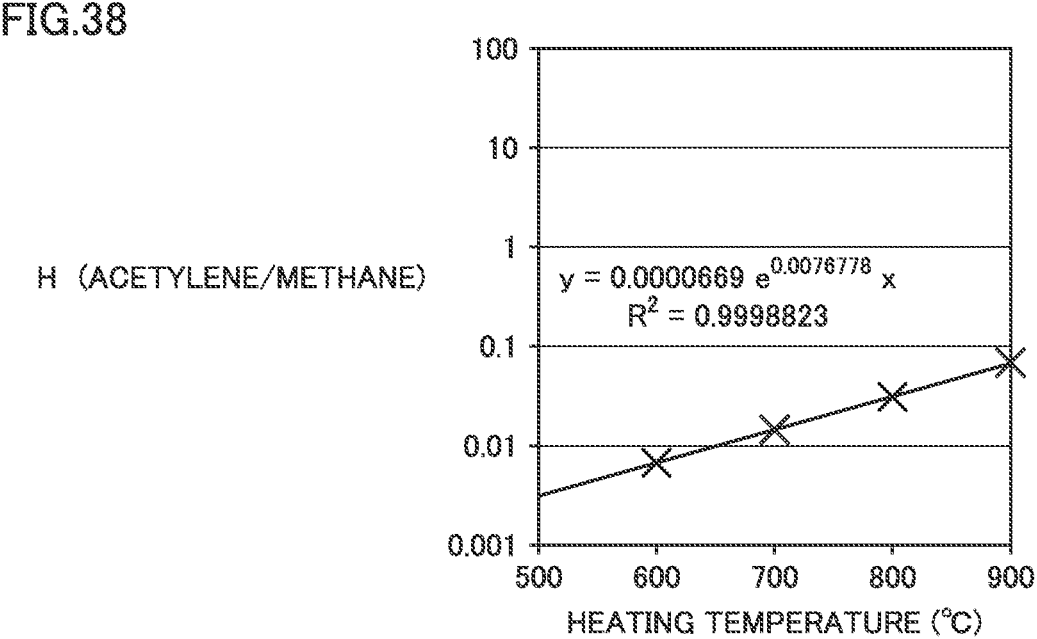
FIG. 38 is a graph showing relation between a gas component concentration ratio and a heating temperature (not higher than 900° C.) shown in Table 3, of natural ester oil.
Figure 39:
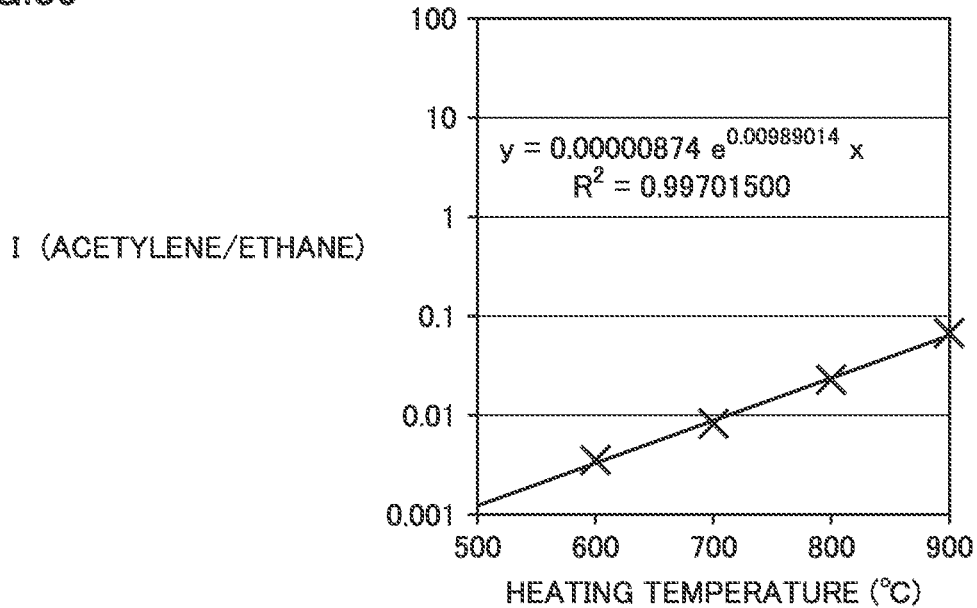
FIG. 39 is a graph showing relation between a gas component concentration ratio and a heating temperature (not higher than 900° C.) shown in Table 3, of natural ester oil.
Figure 40:
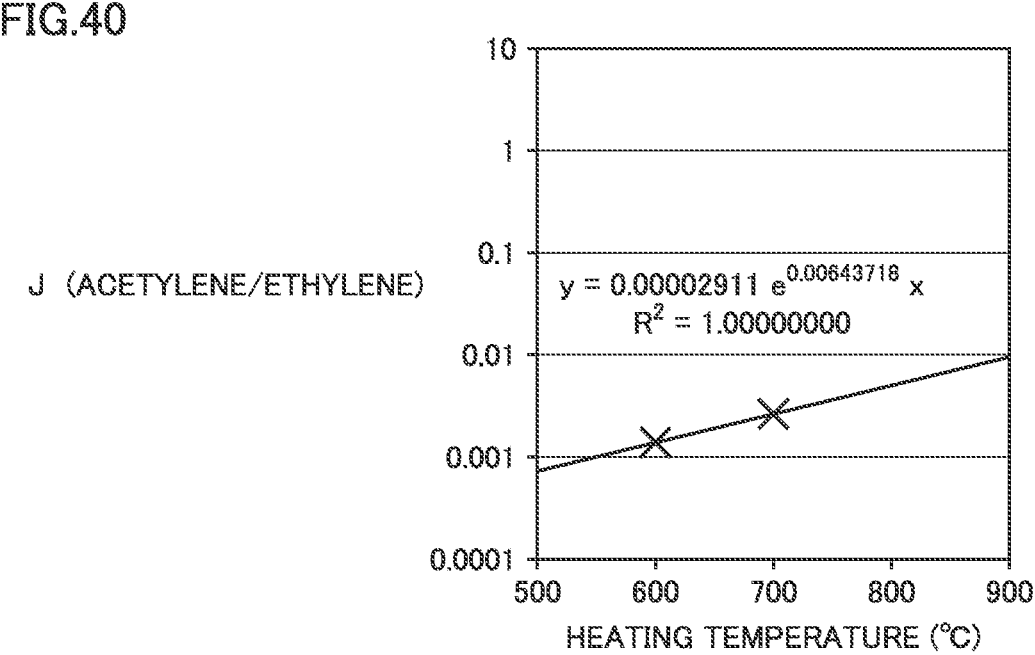
FIG. 40 is a graph showing relation between a gas component concentration ratio and a heating temperature (not higher than 900° C.) shown in Table 3, of natural ester oil.
Figure 41:
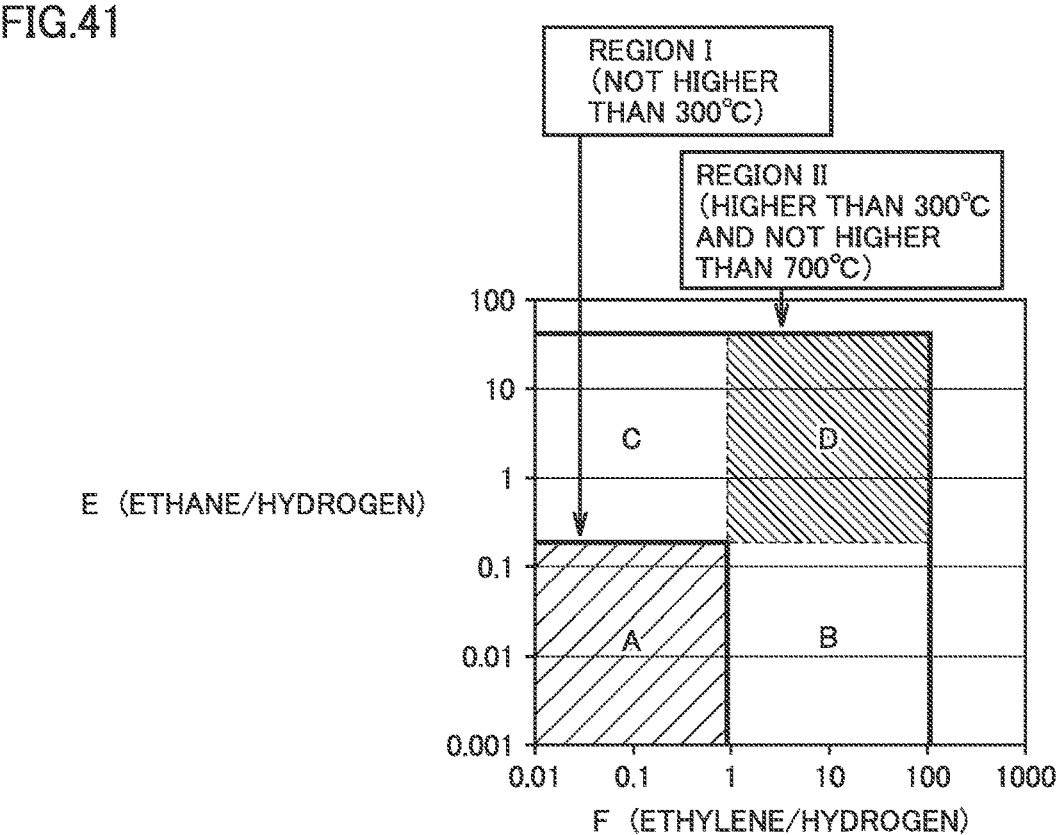
FIG. 41 shows one example of an overheating temperature evaluation diagram for synthetic ester oil.
Figure 42:
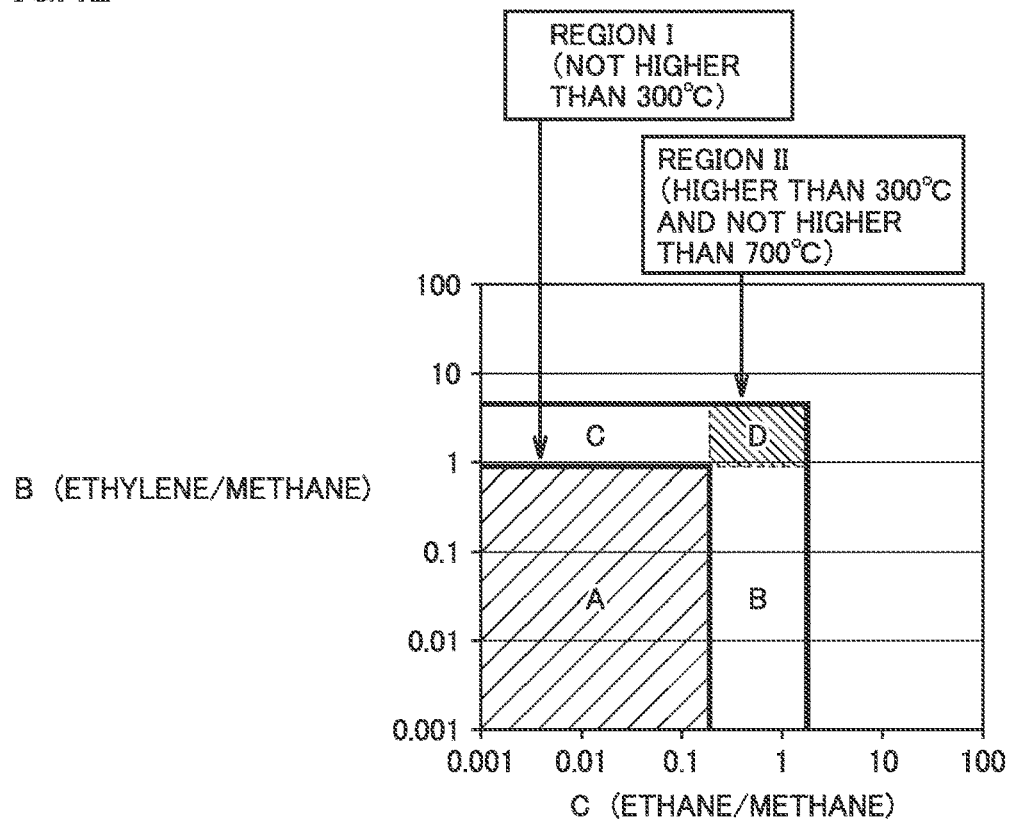
FIG. 42 shows one example of an overheating temperature evaluation diagram for synthetic ester oil.
Figure 43:
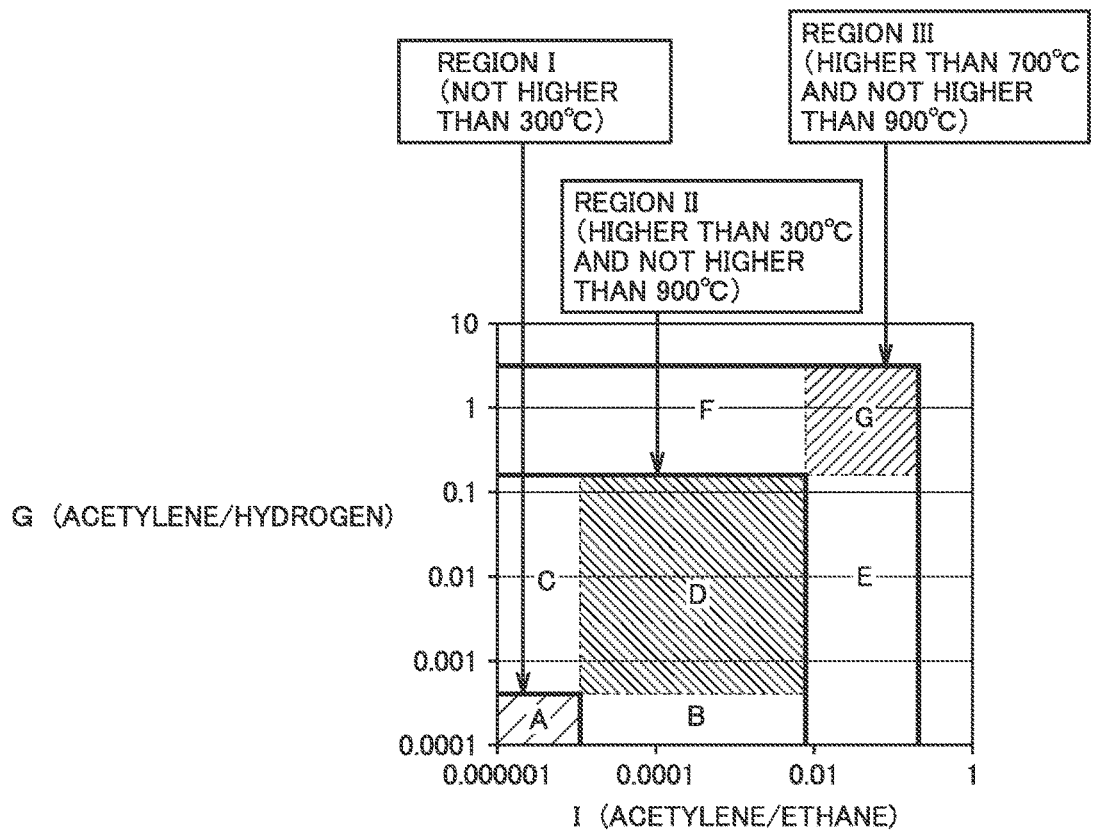
FIG. 43 shows one example of an overheating temperature evaluation diagram for synthetic ester oil.
Figure 44:
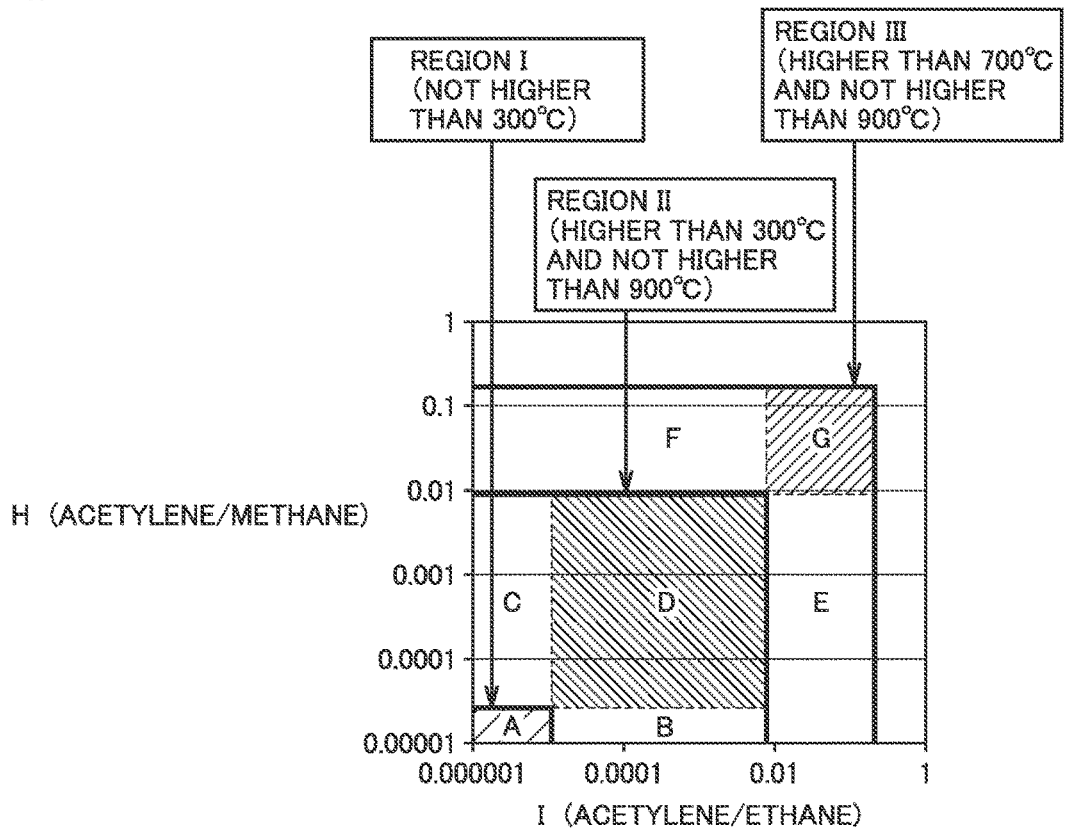
FIG. 44 shows one example of an overheating temperature evaluation diagram for synthetic ester oil.
Figure 45:
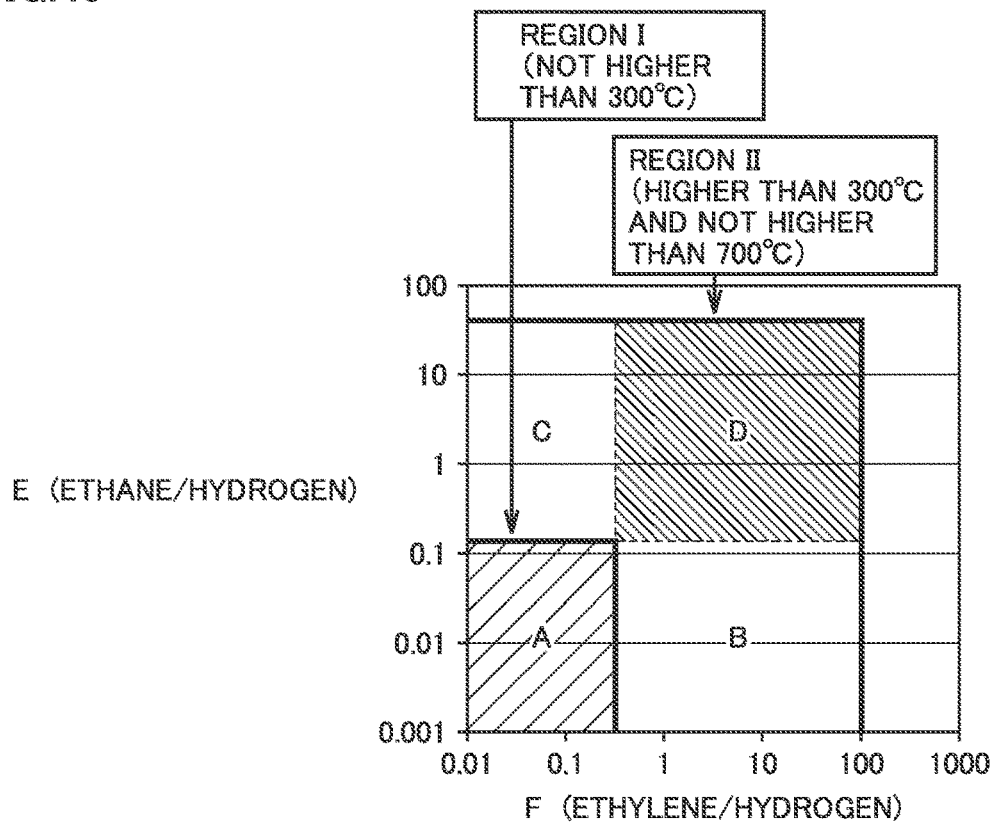
FIG. 45 shows one example of an overheating temperature evaluation diagram for natural ester oil.
Figure 46:
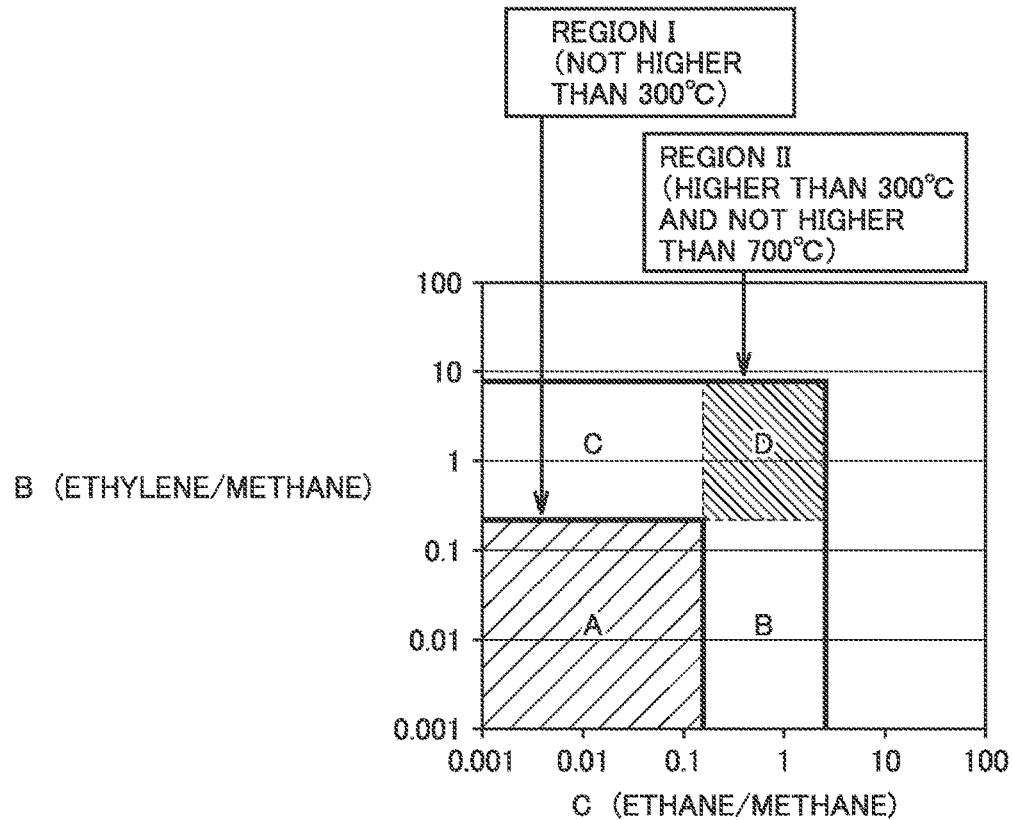
FIG. 46 shows one example of an overheating temperature evaluation diagram for natural ester oil.
Figure 47:
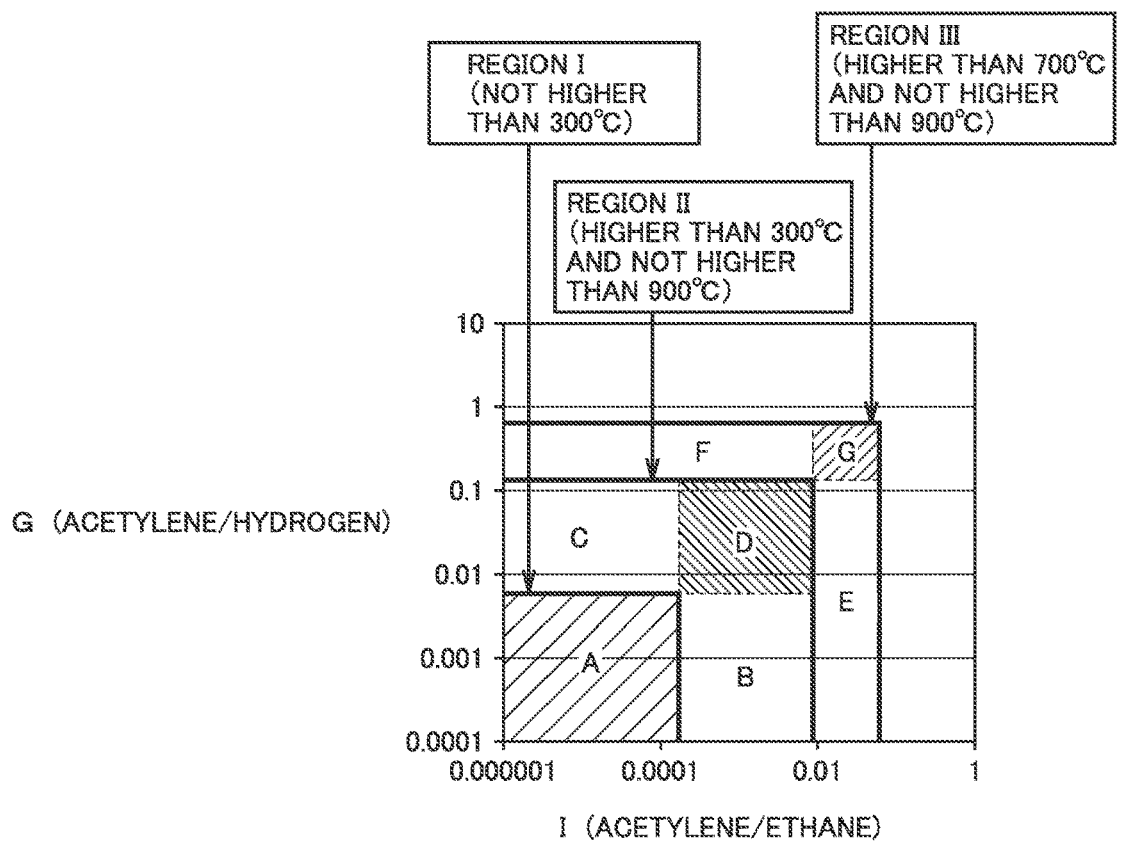
FIG. 47 shows one example of an overheating temperature evaluation diagram for natural ester oil.
Figure 48:
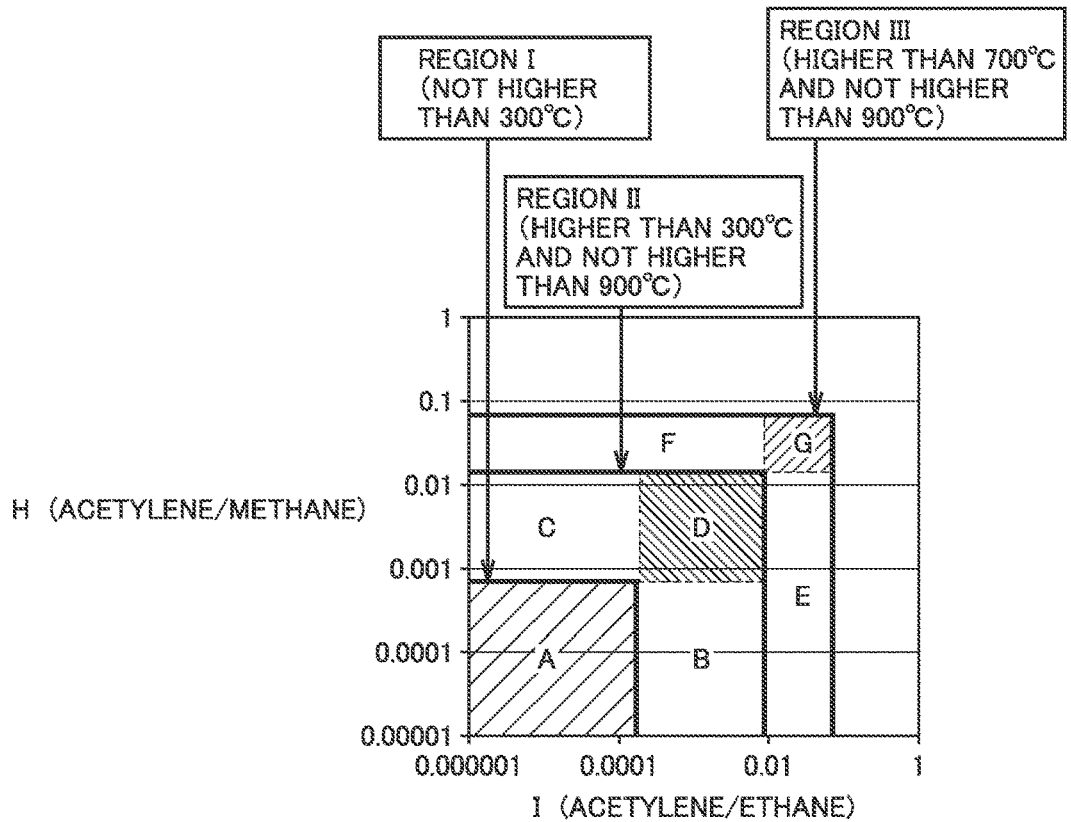
FIG. 48 shows one example of an overheating temperature evaluation diagram for natural ester oil.

An embodiment of the present invention will be described below.

First Embodiment

An estimation method in the present embodiment is a method of estimating an overheating temperature of an oil-immersed electric appliance in which ester oil is used as insulating oil. The overheating temperature refers to a temperature of a temperature increased portion in an oil-immersed electric appliance at the time when temperature increase such as overheat abnormality occurs in the oil-immersed electric appliance.

Examples of the oil-immersed electric appliance include an oil-immersed electric appliance in which coil copper wrapped with coil insulating paper is arranged in ester oil, and specifically include a transformer. Since ester oil is often used in a vehicle-mounted oil-immersed electric appliance (for rail vehicles) with safety being focused on, a diagnosis method in the present embodiment can suitably be used for a vehicle-mounted oil-immersed electric appliance.

Ester oil refers to oil mainly (for example, at least 90 mass %) composed of oil having ester bonds.

Examples of ester oil include polyol ester obtained by esterification between polyalcohol and carboxylic acid and aliphatic ester obtained by esterification between aliphatic carboxylic acid and monoalcohol.

Ester oil is categorized into three types (synthetic ester oil, natural ester oil, and plant-derived ester oil) in Japan and into two types (synthetic ester oil and natural ester oil) abroad.

International Electrotechnical Commission (IEC) defines synthetic ester oil (polyol ester) as consisting of carbon, hydrogen, and oxygen, being synthesized from monovalent or polyvalent alcohol and monobasic or polybasic fatty acid or aromatic acid, and being composed of a mixture of ester including one ester or a plurality of esters (IEC 61099). Natural ester oil (vegetable oil) is defined as vegetable oil obtained from seeds or other appropriate biological materials and composed of triglyceride (IEC 62770).

Table 1 shows types and comparison of exemplary insulating oil. Denotation as A to C in Table 1 mean "A: better than mineral oil, B: equivalent to mineral oil, C: poorer than mineral oil."

TABLE 1

| | | Non-Mineral Oil | | |
|---|---|---|---|---|
| Type of Oil | Mineral Oil Paraffin Base | Silicone Oil | Ester Oil Synthetic | |
| Structure | $CH_3{-}(CH_2)_n{-}CH_3$ | 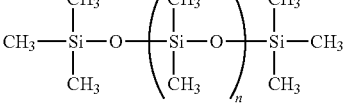 | 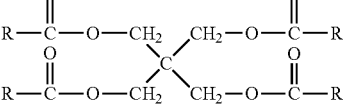 | |
| Source Material | Lubricant | Silane Compound | Polyol | Polyol |
| Biodegradability | No | No | Yes | Yes |
| Flash Point | — | A | A | A |
| Cooling Capability | — | C | C | C |
| Breakdown Voltage | — | B | B | B |

TABLE 1-continued

| | Non-Mineral Oil Ester Oil | |
| --- | --- | --- |
| Type of Oil | Natural | Vegetable Base |
| Structure | $$\begin{array}{c} O \\ \| \\ R-C-O-CH_2 \\ O \\ \| \\ R-C-O-CH_2 \\ O \\ \| \\ R-C-O-CH_2 \end{array}$$ | $$\begin{array}{c} O \\ \| \\ R-C-O-R \end{array}$$ |
| Source Material | Rapseed Oil    Soybean Oil    Sunflower Seed Oil | Palm Oil |
| Biodegradability | Yes    Yes    Yes | Yes |
| Flash Point | A    A    A | B |
| Cooling Capability | C    C    C | B |
| Breakdown Voltage | B    B    B | B |

According to the estimation method in the present embodiment, an overheating temperature is estimated based on a first concentration ratio representing a concentration ratio between two types of gas components contained in ester oil and a second concentration ratio representing a concentration ratio between other two types of gas components contained in the ester oil. The first concentration ratio and the second concentration ratio are selected from a concentration ratio between acetylene and ethane, a concentration ratio between acetylene and hydrogen, a concentration ratio between acetylene and methane, and a concentration ratio between acetylene and ethylene.

Since these concentration ratios associated with acetylene extremely highly correlate with a heating temperature of ester oil, an overheating temperature can highly accurately be estimated by adopting acetylene as an indicator. Since the concentration ratio associated with acetylene highly correlates with a temperature also under a high-temperature condition (for example, exceeding 700° C.), an overheating temperature can highly accurately be estimated even when high-temperature overheat abnormality occurs.

These concentration ratios are combination of concentration ratios between two types of gas components which have been found in the studies conducted by the present inventors to particularly be large in variation with increase in temperature of ester oil in an example where ester oil is natural ester oil. An error in diagnosis can be lessened by estimating an overheating temperature based on these concentration ratios and an overheating temperature can highly accurately be estimated.

One of the first concentration ratio and the second concentration ratio is preferably a concentration ratio between acetylene and ethane. In this case, the concentration ratio between acetylene and ethane is largest in variation with increase in temperature of ester oil among the above three concentration ratios, and therefore an overheating temperature can further highly accurately be estimated.

Generation of acetylene from silicone oil is less likely than from ester oil. Acetylene is not generated up to approximately 800° C. even though overheat abnormality occurs. Therefore, acetylene cannot be used as an indicator in estimation of an overheating temperature of an oil-immersed electric appliance in which silicone oil is used as insulating oil. In contrast, the present inventors have found that acetylene can be used as an indicator in estimation of an overheating temperature in an oil-immersed electric appliance in which ester oil is used as insulating oil.

The first concentration ratio and the second concentration ratio are preferably selected from the concentration ratio between acetylene and ethane, the concentration ratio between acetylene and methane, and the concentration ratio between acetylene and ethylene. In this case, hydrogen is not adopted as the indicator. Therefore, there is no influence by Stray Gassing which will be described later and an overheating temperature can further highly accurately be estimated.

The concentration ratio between acetylene and ethane is preferably a concentration ratio of acetylene to ethane (acetylene/ethane). The concentration ratio between acetylene and hydrogen is preferably a concentration ratio of acetylene to hydrogen (acetylene/hydrogen). The concentration ratio between acetylene and methane is preferably a concentration ratio of acetylene to methane (acetylene/methane). The concentration ratio between acetylene and ethylene is preferably a concentration ratio of acetylene to ethylene (acetylene/ethylene).

Though a ratio calculated by interchanging a numerator and a denominator in these ratios can also be adopted as an indicator in estimation of an overheating temperature, such a ratio represents relation in inverse proportion to a temperature of ester oil. Therefore, it becomes difficult to read a scale on an overheating temperature evaluation diagram, and for ease of reading, the order of scales on the overheating temperature evaluation diagram should be reversed. Therefore, it is convenient to adopt the above-described concentration ratios as the indicator.

In a specific diagnosis method, an overheating temperature evaluation diagram in which the abscissa represents the first concentration ratio and the ordinate represents the second concentration ratio is divided into areas (see FIGS. 43, 44, 47, and 48 which will be described later), and an overheating temperature is estimated based on in which area in the overheating temperature evaluation diagram a plot corresponding to measurement values of the first concentration ratio and the second concentration ratio is located.

In preparing an overheating temperature evaluation diagram, for example, a test system simulating overheat abnormality of an oil-immersed electric appliance in which ester oil is used is constructed (see FIG. 50 which will be described later), the ester oil is heated, and a gas component dissolved in the ester oil is analyzed. An overheating temperature evaluation diagram can be prepared based on results of analysis (see FIGS. 41 to 48 which will be described later).

An overheating temperature of an ester-oil-immersed electric appliance can be estimated by measuring a concentration ratio between gas components in the ester oil in the oil-immersed electric appliance and applying results of measurement to the overheating temperature evaluation diagram. For example, whether or not an overheating temperature has exceeded a predetermined threshold temperature can be estimated.

When an overheating temperature estimated with the method of estimating an overheating temperature in the present embodiment is higher than a specific threshold value, it may be determined that any measures should urgently be taken so that occurrence of overheat abnormality can appropriately be addressed.

A concentration in oil of a gas component generated due to an internal fault in an oil-immersed electric appliance is different depending on a duration of a fault and an area of an abnormal site in addition to a temperature of an abnormal portion, and it is difficult to estimate a state of abnormality (an overheating temperature) only based on a concentration of a gas component. A concentration ratio between a plurality of gas components in oil, however, is not dependent on a duration of a fault or an area of an abnormal site but dependent on a temperature of an abnormal portion. Therefore, it is effective to use a concentration ratio between gas components in estimation of an overheating temperature (a temperature of an abnormal portion).

In order to perform a diagnosis method in the present embodiment, initially, gas (sample gas) including gas which exists as being dissolved in insulating oil in an oil-immersed electric appliance should be extracted. Examples of a method of extracting sample gas from insulating oil include a method of agitating oil in a gastight container (or a hermetically sealed oil-immersed electric appliance) and sampling sample gas which volatilizes into an upper space (a head space) in the gastight container, a method of producing a vacuum in a space above oil accommodated in a gastight container and having oil injected into the vacuum space, or a method of extracting sample gas by bubbling with inert gas such as argon gas in oil.

In order to know influence by aging of an internally coexisting material or ester oil concurrently with analysis of gas in oil, as preliminary examination, a material used in the inside of an oil-immersed electric appliance may be examined and characteristics of ester oil may be determined.

Though two indicators are used in the present embodiment, the diagnosis method in the present embodiment also encompasses diagnosis with yet another indicator in addition to the two indicators above. For example, when three indicators in total are used, a three-dimensional overheating temperature evaluation diagram can be prepared so that an overheating temperature can be estimated based on that overheating temperature evaluation diagram.

(Gas Analyzer)

An exemplary gas analyzer which can be used for analysis of a gas component in the method of estimating an overheating temperature according to the present invention will be described below.

The gas analyzer mainly includes a gas flow path through which sample gas flows and an optical detection system which detects light in a wavelength range including any wavelength in an absorption band of a measurement target component.

The optical detection system includes as basic features, a gas cell connected to the flow path, a light source which emits light to gas to be analyzed in the gas cell, and an optical detector which detects light which has passed through the gas to be analyzed. The optical detector may detect not only light which has passed through gas to be analyzed but also light reflected by the gas to be analyzed. Instead of the optical detector, a thermal conductivity detector (TCD) or a flame ionization detector (FID) may be employed.

By finding variation in light transmittance depending on presence/absence of a gas component based on intensity of light detected by the optical detector, a concentration of each gas component can be measured with the use of a calibration curve prepared in advance.

The optical detection system optically analyzes gas introduced into a gas cell provided in a gas flow path. The gas introduced into the gas flow path is normally a gas mixture containing sample gas taken from insulating oil and carrier gas for introduction of the sample gas into the gas cell. Though the carrier gas is not particularly limited, air in atmosphere is preferably used because it can readily be supplied without the need for supply of special gas. Only the sample gas may be introduced into the gas flow path without using carrier gas.

In order to individually measure a plurality of types of gas components contained in insulating oil (ester oil), for example, a gas separation column can be used. A concentration of each gas component can be measured by firstly feeding sample gas (gas contained as being dissolved in insulating oil (sample oil) filled in an oil-immersed electric appliance and taken by a small amount) to a gas separation column to physically or chemically separate the sample gas into gas components and introducing the resultant sample gas into a gas cell.

The gas separation column is an instrument for separation of each measurement target component by making use of a difference in time period required for each measurement target component to pass through sample gas. Various known separation columns used for gas chromatography can be employed as the gas separation column, and a gas separation column is selected as appropriate in accordance with a type of a measurement target component to be analyzed.

A light source is not particularly limited so long as the light source can emit light including an absorption band of a measurement target component. When light corresponding to the absorption band of the measurement target component is infrared light, an infrared light source is preferred. Infrared light emitted from an infrared light source is more preferably mid-infrared light (having a wavelength approximately from 3 to 5 μm).

For example, when sample gas contains a plurality of measurement target components and absorption bands of the measurement target components are close to one another, in order to measure individual measurement target components, only light having a wavelength not overlapping with the absorption band of another measurement target component should be detected. Therefore, an optical filter which allows passage of only light within a desired wavelength range but does not allow passage of light other than that may be provided between the light source and the optical detector. Alternatively, a light source which emits only light within a desired wavelength range but does not emit light other than that (a narrow-band light source) may be employed as the light source. Examples of the narrow-band light source include an LED light source. In order to improve detection sensitivity, a wavelength of light to be detected preferably includes a maximum absorption wavelength of a measurement target component.

Not only (1) a method of measuring gas in insulating oil with an analyzer mounted on an oil-immersed electric appliance (transformer) (online) as above but also (2) a method of measuring gas in insulating oil by taking the insulating oil from a lower portion of the oil-immersed electric appliance and conducting measurement with an analyzer provided at another location (offline) can be used as a method of analyzing gas in insulating oil (see, for example, Denki Kyodo Kenkyu, Vol. 65, No. 1, "Denryoku-you Hen'atsuki Kaishu Guideline," Section II, Chapter 2, 2-2 to 2-5). Since a result of measurement can be monitored online at any time with the analyses method (1), this method is advantageous in early diagnosis of overheat abnormality. In general, however, the analysis method (2) is often used so that analysis higher in sensitivity and accuracy can be achieved.

Second Embodiment

A method of estimating an overheating temperature of an oil-immersed electric appliance in the present embodiment is different from the first embodiment in that when ester oil does not contain acetylene, the first concentration ratio and the second concentration ratio are selected from a concentration ratio between ethylene and hydrogen, a concentration ratio between ethane and hydrogen, a concentration ratio between ethylene and methane, and a concentration ratio between methane and ethane.

When ester oil contains acetylene, the first concentration ratio and the second concentration ratio are selected from the concentration ratio between acetylene and ethane, the concentration ratio between acetylene and hydrogen, and the concentration ratio between acetylene and methane as in the first embodiment.

Since the present embodiment is otherwise basically the same as the first embodiment, redundant description will not be provided.

An internal fault in an oil-immersed electric appliance may be discharging and overheating, and acetylene generated during discharging which may develop to a particularly serious internal fault serves as indicator gas important in determination as to an internal fault based on analysis of gas in oil.

When an overheating temperature of an oil-immersed electric appliance is lower than 600° C., however, generation of acetylene is less likely and it is difficult to diagnose based on acetylene, an internal fault in the oil-immersed electric appliance in which ester oil is used. Therefore, in such a case, an overheating temperature is estimated preferably based on a concentration ratio between gas components other than acetylene.

The concentration ratio between ethylene and hydrogen, the concentration ratio between ethane and hydrogen, the concentration ratio between ethylene and methane, and the concentration ratio between ethane and methane are combinations of concentration ratios between two types of gas components found in the studies conducted by the present inventors to particularly be large in variation with increase in temperature of ester oil. By estimating an overheating temperature based on these concentration ratios, an error in diagnosis can be lessened and an overheating temperature can highly accurately be estimated.

One of the first concentration ratio and the second concentration ratio is preferably the concentration ratio between ethylene and hydrogen or the concentration ratio between ethane and hydrogen. The first concentration ratio and the second concentration ratio are more preferably the concentration ratio between ethylene and hydrogen and the concentration ratio between ethane and hydrogen. In this case, since the concentration ratio between ethylene and hydrogen and the concentration ratio between ethane and hydrogen are particularly large in variation with increase in temperature of ester oil among concentration ratios A to F (between ethane and ethylene, between ethylene and methane, between ethane and methane, between methane and hydrogen, between ethane and hydrogen, and between ethylene and hydrogen), an overheating temperature can further highly accurately be estimated.

The concentration ratio between ethylene and hydrogen is preferably a concentration ratio of ethylene to hydrogen (ethylene/hydrogen). The concentration ratio between ethane and hydrogen is preferably a concentration ratio of ethane to hydrogen (ethane/hydrogen). The concentration ratio between ethylene and methane is preferably a concentration ratio of ethylene to methane (ethylene/methane). The concentration ratio between methane and ethane is preferably a concentration ratio of methane to ethane (methane/ethane).

Though a ratio calculated by interchanging a numerator and a denominator in these ratios can also be adopted as an indicator in estimation of an overheating temperature, such a ratio represents relation in inverse proportion to a temperature of ester oil. Therefore, it becomes difficult to read a scale on an overheating temperature evaluation diagram, and for ease of reading, the order of scales on the overheating temperature evaluation diagram should be reversed. Therefore, it is convenient to adopt the above-described concentration ratios as the indicator.

In the present embodiment as well, as in the first embodiment, an overheating temperature evaluation diagram in which the abscissa represents the first concentration ratio and the ordinate represents the second concentration ratio is divided into areas, and an overheating temperature is estimated based on in which area in the overheating temperature evaluation diagram a plot corresponding to measurement values of the first concentration ratio and the second concentration ratio is located.

Figure 49:
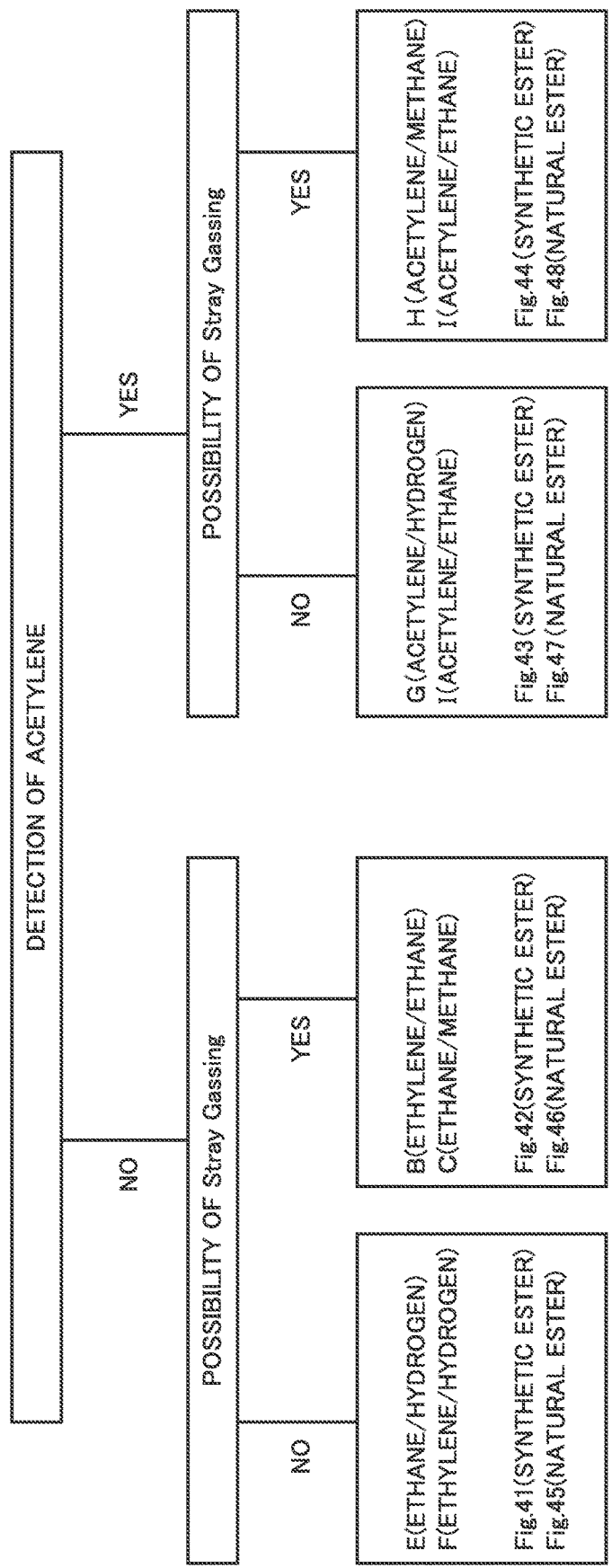
FIG. 49 is a flowchart showing a method of estimating an overheating temperature in a second embodiment.

In the present embodiment, as shown in FIG. 49, an overheating temperature evaluation diagram used for estimation is selected from among FIGS. 41 to 48 in accordance with a result of analysis of gas components actually contained in ester oil in an oil-immersed electric appliance (whether or not acetylene is detected and the possibility of Stray Gassing).

Possibility of Stray Gassing can be determined, for example, with reference to criteria for Stray Gassing in mineral oil described on page 15 (Table 18) in "CIGRE, 296, Joint Task Force D1.01/A2.11, Recent developments in DGA interpretation, June 2006," with whether or not hydrogen, methane, and/or ethane is/are generated and a ratio between methane and hydrogen being defined as indicators.

EXAMPLES

First Test Example

Figure 50:
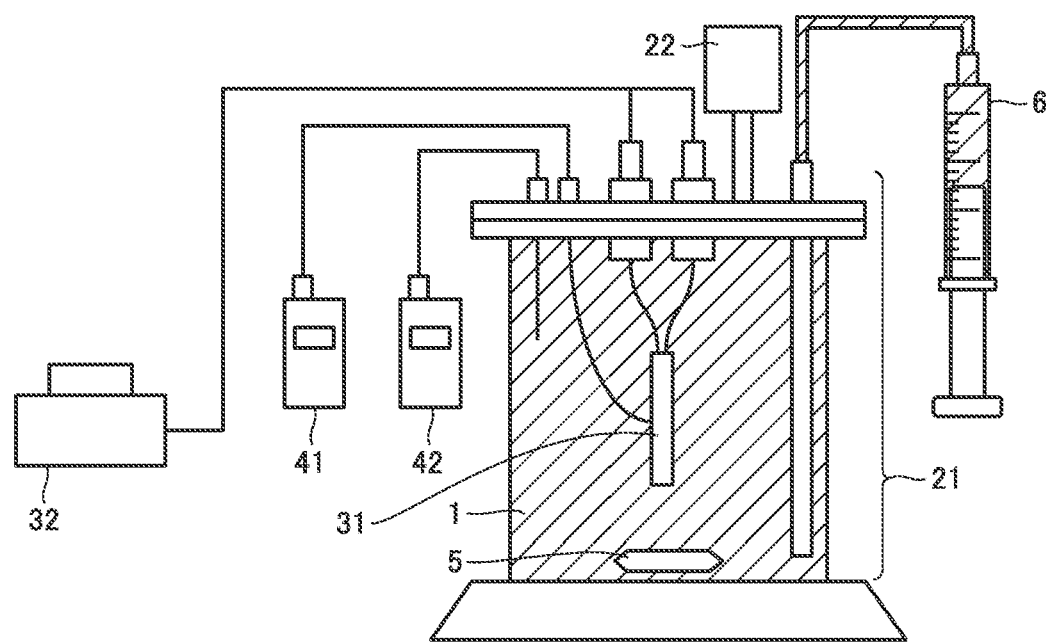
FIG. 50 is a schematic diagram of a test system simulating overheat abnormality of an oil-immersed electric appliance in which ester oil is used in a first test example.

In order to simulate a (local) overheating state which occurs in an oil-immersed electric appliance in which ester oil is used as insulating oil, a heater 31 was set in a test vessel 21 and ester oil 1 was heated (see FIG. 50). Test vessel 21 was provided with a conservator 22 and heater 31 was powered by an AC power supply 32.

In the present test example, synthetic ester oil and natural ester oil as ester oil were analyzed.

Temperatures of heater 31 and ester oil 1 were measured with a thermometer 41 and a thermometer 42, respectively. Heating by heater 31 was controlled based on measurement with thermometers 41 and 42, and a temperature of heater 31 was maintained at 100° C., 200° C., 300° C., 400° C., 500° C., 600° C., 700° C., 800° C., and 900° C. In order to uniformly dissolve a gas component resulting from thermal decomposition of the ester oil, ester oil 1 was agitated with an agitator 5. After heating for ten minutes at each temperature, ester oil 1 was sampled with a removable oil sampling syringe 6.

A concentration of each of four types of gas components (hydrogen, methane, ethane, ethylene, and acetylene) contained in the ester oil was measured by extracting a gas component dissolved in the taken ester oil by bubbling of inert gas and measuring the extracted gas component with a gas chromatograph incorporating a detector (TCD and FID). Table 2 shows results of measurement.

TABLE 2

| Type of Oil | Gas Component | Heating Temperature (° C.) | | | | | | | | | |
|---|---|---|---|---|---|---|---|---|---|---|---|
| | | 25 | 100 | 200 | 300 | 400 | 500 | 600 | 700 | 800 | 900 |
| Synthetic Ester Oil | Hydrogen (ppm) | 0 | 0 | 0 | 0 | 18 | 79 | 168 | 402 | 1323 | 2915 |
| | Methane (ppm) | 0 | 0 | 0 | 0 | 30 | 510 | 2359 | 7464 | 28283 | 42460 |
| | Ethane (ppm) | 0 | 0 | 0 | 0 | 7 | 431 | 3160 | 9661 | 31943 | 33280 |
| | Ethylene (ppm) | 0 | 0 | 0 | 3 | 39 | 1043 | 8054 | 31159 | 144680 | 211150 |
| | Acetylene (ppm) | 0.0 | 0.0 | 0.0 | 0.0 | 0.0 | 0.0 | 4.5 | 74.0 | 1320.0 | 6315.0 |
| Natural Ester Oil | Hydrogen (ppm) | 0 | 0 | 0 | 4 | 25 | 168 | 564 | 1133 | 2355 | 4418 |
| | Methane (ppm) | 0 | 0 | 0 | 3 | 55 | 864 | 4673 | 13406 | 24748 | 40183 |
| | Ethane (ppm) | 0 | 0 | 0 | 1 | 8 | 918 | 8940 | 23525 | 33082 | 40263 |
| | Ethylene (ppm) | 0 | 0 | 0 | 0 | 22 | 1402 | 22746 | 73232 | 135047 | 197229 |
| | Acetylene (ppm) | 0.0 | 0.0 | 0.0 | 0.0 | 0.0 | 0.0 | 31.5 | 193.1 | 759.1 | 2721.3 |

Table 3 shows results of calculation of a concentration ratio at each temperature from a concentration measurement value of each gas component in ester oil shown in Table 2, as concentration ratios A to J between gas components shown in Table 3.

TABLE 3

| Type of Oil | Concentration Ratio Between Gas Components | Heating Temperature (° C.) | | | | | | | | | |
|---|---|---|---|---|---|---|---|---|---|---|---|
| | | 25 | 100 | 200 | 300 | 400 | 500 | 600 | 700 | 800 | 900 |
| Synthetic Ester Oil | A (Ethane/Ethylene) | — | — | — | — | 0.179487 | 0.412752 | 0.392290 | 0.310060 | 0.220780 | 0.157613 |
| | B (Ethylene/Methane) | — | — | — | — | 1.300000 | 2.045098 | 3.414882 | 4.174784 | 5.115531 | 4.972916 |
| | C (Ethane/Methane) | — | — | — | — | 0.233333 | 0.844118 | 1.339623 | 1.294433 | 1.129409 | 0.783797 |
| | D (Methane/Hydrogen) | — | — | — | — | 1.714286 | 6.496815 | 14.080597 | 18.589041 | 21.385633 | 14.566038 |
| | E (Ethane/Hydrogen) | — | — | — | — | 0.400000 | 5.484076 | 18.862687 | 24.062267 | 24.153119 | 11.416810 |
| | F (Ethylene/Hydrogen) | — | — | — | — | 2.228571 | 13.286624 | 48.083582 | 77.605230 | 109.398866 | 72.435678 |
| | G (Acetylene/Hydrogen) | — | — | — | — | — | — | 0.026866 | 0.184309 | 0.998110 | 2.166381 |
| | H (Acetylene/Methane) | — | — | — | — | — | — | 0.001908 | 0.009915 | 0.046672 | 0.148728 |
| | I (Acetylene/Ethane) | — | — | — | — | — | — | 0.001424 | 0.007660 | 0.041324 | 0.189754 |
| | J (Acetylene/Ethylene) | — | — | — | — | — | — | 0.000559 | 0.002375 | 0.009124 | 0.029908 |
| Natural Ester Oil | A (Ethylene/Ethane) | — | — | — | — | 2.933333 | 1.527520 | 2.544295 | 3.112944 | 4.082175 | 4.898517 |
| | B (Ethylene/Methane) | — | — | — | — | 0.403670 | 1.622106 | 4.867537 | 5.462629 | 5.456865 | 4.908331 |
| | C (Ethane/Methane) | — | — | — | 0.200000 | 0.137615 | 1.061921 | 1.913118 | 1.754811 | 1.336754 | 1.002003 |
| | D (Methane/Hydrogen) | — | — | — | 0.625000 | 2.224490 | 5.158209 | 8.285461 | 11.837528 | 10.508705 | 9.095179 |
| | E (Ethane/Hydrogen) | — | — | — | 0.125000 | 0.306122 | 5.477612 | 15.851064 | 20.772627 | 14.047558 | 9.113400 |
| | F (Ethylene/Hydrogen) | — | — | — | — | 0.897959 | 8.367164 | 40.329787 | 64.664018 | 57.344586 | 44.642146 |
| | G (Acetylene/Hydrogen) | — | — | — | — | — | — | 0.055851 | 0.170464 | 0.322335 | 0.615946 |
| | H (Acetylene/Methane) | — | — | — | — | — | — | 0.006741 | 0.014400 | 0.030673 | 0.067722 |
| | I (Acetylene/Ethane) | — | — | — | — | — | — | 0.003523 | 0.008206 | 0.022946 | 0.067587 |
| | J (Acetylene/Ethylene) | — | — | — | — | — | — | 0.001385 | 0.002636 | 0.005621 | 0.013797 |

FIGS. 1 to 40 are graphs each showing relation between a concentration ratio between gas components and a heating temperature shown in Table 3. The graph shows a regression line found with the least square method based on each concentration ratio shown in Table 3, and shows a regression expression (an approximation expression) and a coefficient of correlation ($R^2$).

Table 4 summarizes approximation expressions ($y=ae^{kx}$) shown in FIGS. 1 to 40. k in Table 4 represents a constant k when the regression expression is expressed as $y=ae^{kx}$ (where e represents a base of a natural logarithm and a and k each represent a constant), and corresponds to an inclination in logarithmic expression of the y axis as in the graphs shown in FIGS. 1 to 40.

TABLE 4

| | | Range of Heating Temperatures: 100° C. to 700° C. | | | | Range of Heating Temperatures: 100° C. to 900° C. | | | |
|---|---|---|---|---|---|---|---|---|---|
| Type of Oil | Concentration Ratio Between Gas Components | FIG. | Approximation Expression | Coefficient of Correlation | k × 100000 | FIG. | Approximation Expression | Coefficient of Correlation | k × 100000 |
| Synthetic Ester Oil | A (Ethane/Ethylene) | 1 | $y = 0.129\ e^{0.00159\ x}$ | 0.290  0.795 | 159 | 11 | $y = 0.435\ e^{-0.000789\ x}$ | 0.132  0.550 | −79 |
| | B (Ethylene/Methane) | 2 | $y = 0.273\ e^{0.00401\ x}$ | 0.972 | 401 | 12 | $y = 0.523\ e^{0.00276\ x}$ | 0.889 | 276 |
| | C (Ethane/Methane) | 3 | $y = 0.0351\ e^{0.00560\ x}$ | 0.781 | 560 | 13 | $y = 0.228\ e^{0.00197\ x}$ | 0.318 | 197 |
| | D (Methane/Hydrogen) | 4 | $y = 0.0941\ e^{0.00792\ x}$ | 0.919 | 792 | 14 | $y = 0.660\ e^{0.00416\ x}$ | 0.670 | 416 |
| | E (Ethane/Hydrogen) | 5 | $y = 0.00330\ e^{0.0135\ x}$ | 0.866 | 1350 | 15 | $y = 0.150\ e^{0.00613\ x}$ | 0.529 | 613 |
| | F (Ethylene/Hydrogen) | 6 | $y = 0.0257\ e^{0.0119\ x}$ | 0.943 | 1190 | 16 | $y = 0.345\ e^{0.00692\ x}$ | 0.762 | 692 |
| | G (Acetylene/Hydrogen) | 7 | $y = 0.000000258\ e^{0.193\ x}$ | 1.000  1.000 | 1930 | 17 | $y = 0.00000465\ e^{0.0149\ x}$ | 0.969  0.990 | 1490 |
| | H (Acetylene/Methane) | 8 | $y = 0.0000000969\ e^{0.0165\ x}$ | 1.000 | 1650 | 18 | $y = 0.000000330\ e^{0.0146\ x}$ | 0.994 | 1460 |
| | I (Acetylene/Ethane) | 9 | $y = 0.0000000589\ e^{0.0168\ x}$ | 1.000 | 1680 | 19 | $y = 0.0000000801\ e^{0.0164\ x}$ | 0.999 | 1640 |
| | J (Acetylene/Ethylene) | 10 | $y = 0.0000000947\ e^{0.0145\ x}$ | 1.000 | 1450 | 20 | $y = 0.000000205\ e^{0.0133\ x}$ | 0.998 | 1330 |
| Natural Ester Oil | A (Ethylene/Ethane) | 21 | $y = 1.67\ e^{0.000688\ x}$ | 0.075  0.758 | 69 | 31 | $y = 1.03\ e^{0.00163\ x}$ | 0.569  0.642 | 163 |
| | B (Ethylene/Methane) | 22 | $y = 0.0152\ e^{0.00891\ x}$ | 0.902 | 891 | 32 | $y = 0.136\ e^{0.00464\ x}$ | 0.678 | 464 |
| | C (Ethane/Methane) | 23 | $y = 0.0192\ e^{0.00698\ x}$ | 0.787 | 698 | 33 | $y = 0.0900\ e^{0.00353\ x}$ | 0.516 | 353 |
| | D (Methane/Hydrogen) | 24 | $y = 0.102\ e^{0.00720\ x}$ | 0.936 | 720 | 34 | $y = 0.376\ e^{0.00427\ x}$ | 0.743 | 427 |
| | E (Ethane/Hydrogen) | 25 | $y = 0.00195\ e^{0.0142\ x}$ | 0.919 | 1420 | 35 | $y = 0.0339\ e^{0.00780\ x}$ | 0.668 | 780 |
| | F (Ethylene/Hydrogen) | 26 | $y = 0.00429\ e^{0.0144\ x}$ | 0.930 | 1440 | 36 | $y = 0.160\ e^{0.00737\ x}$ | 0.678 | 737 |
| | G (Acetylene/Hydrogen) | 27 | $y = 0.0000691\ e^{0.0112\ x}$ | 1.000  1.000 | 1120 | 37 | $y = 0.000583\ e^{0.00784\ x}$ | 0.979  0.993 | 784 |
| | H (Acetylene/Methane) | 28 | $y = 0.0000709\ e^{0.00759\ x}$ | 1.000 | 759 | 38 | $y = 0.0000669\ e^{0.00768\ x}$ | 1.000 | 768 |
| | I (Acetylene/Ethane) | 29 | $y = 0.0000221\ e^{0.00845\ x}$ | 1.000 | 845 | 39 | $y = 0.00000874\ e^{0.00989\ x}$ | 0.997 | 989 |
| | J (Acetylene/Ethylene) | 30 | $y = 0.0000291\ e^{0.00644\ x}$ | 1.000 | 644 | 40 | $y = 0.0000132\ e^{0.00765\ x}$ | 0.995 | 765 |

FIGS. 1 to 10 each show relation between a gas component concentration ratio and a heating temperature in a range of heating temperatures from 100 to 700° C., of synthetic ester oil. FIGS. 11 to 20 each show relation between a gas component concentration ratio and a heating temperature in a range of heating temperatures from 100 to 900° C., of the same synthetic ester oil.

FIGS. 21 to 30 each show relation between a gas component concentration ratio and a heating temperature in a range of heating temperatures from 100 to 700° C., of natural ester oil. FIGS. 31 to 40 each show relation between a gas component concentration ratio and a heating temperature in a range of heating temperatures from 100 to 900° C., of the same natural ester oil.

(Selection of Indicator for Estimation of Overheating Temperature)

It is considered that, as an inclination of an approximation expression representing relation between a heating temperature and a concentration ratio between gas components shown in Table 4 (FIGS. 1 to 40) is greater and correlation (coefficient of correlation) is higher, an overheating temperature of an oil-immersed electric appliance can further highly accurately be estimated by using the concentration ratio.

Some concentration ratios between gas components among the results of actual analysis of the gas components in ester oil in the oil-immersed electric appliance may be inappropriate as an indicator for estimation of an overheating temperature. For example, in a transformer in which ester oil is used as insulating oil, an example in which no acetylene is detected (an overheating temperature is low) is observed. In such a case, an overheating temperature should be estimated with a gas component other than acetylene being defined as an indicator.

Stray Gassing (a phenomenon that a large amount of flammable gas is generated due to overheating in a region relatively lower in temperature than in overheat abnormality and a large amount of hydrogen is mainly generated) is also observed. Regardless of occurrence of a fault such as overheat abnormality, hydrogen may be generated over time, for example, also from insulating oil heated in a region relatively lower in temperature than in overheat abnormality, a triazole derivative (Irgamet®) added to insulating oil as an antioxidant, or an internally coexisting material in an oil-immersed electric appliance. In such a case, an overheating temperature should be estimated with the use of indicator gas other than hydrogen.

Therefore, with categorization being made depending on presence/absence of acetylene and the possibility of Stray Gassing, in each case, a concentration ratio high in correlation of an approximation expression showing relation between a heating temperature and a concentration ratio between gas components and in inclination was selected as the indicator for estimation of an overheating temperature, from among combinations of ratios of concentration in oil in Table 4.

The concentration ratios associated with acetylene (corresponding to FIGS. 7 to 10 and 27 to 30) among the results of heating tests from 100° C. to 700° C. in Table 4 were excluded from the indicator, because there were only two pieces of data (600° C. and 700° C.). Though Table 4 shows the coefficient of correlation of 1.000, correlation cannot be concluded as being high because there are only two pieces of data.

The combinations of concentration ratios not associated with acetylene (corresponding to FIGS. 11 to 16 and 31 to 36) among the results of heating tests from 100° C. to 900° C. were excluded from the indicator, because these concentration ratios tend to peak out when the heating temperature is 800° C. or higher and the coefficient of correlation in the approximation expression is low.

Therefore, the concentration ratio between gas components to serve as the indicator for estimation of an overheating temperature was selected from among the combinations of concentration ratios not associated with acetylene (corresponding to FIGS. 1 to 6 and 21 to 26) among the results of the heating tests from 100° C. to 700° C. shown in Table 4 (see Table 5) and the concentration ratios associated with acetylene (corresponding to FIGS. 17 to 20 and 37 to 40) among the results of the heating tests from 100° C. to 900° C. shown in Table 4 (see Table 6). Table 7 shows selected concentration ratios between gas components to serve as the indicator for estimation of an overheating temperature.

TABLE 5

| Type of Oil | Concentration Ratio Between Gas Components | FIG. | Approximation Expression | Coefficient of Correlation | | k × 100000 |
|---|---|---|---|---|---|---|
| Synthetic Ester Oil | A (Ethane/Ethylene) | 1 | $y = 0.129\ e^{0.00159\ x}$ | 0.290 | 0.795 | 159 |
| | B (Ethylene/Methane) | 2 | $y = 0.273\ e^{0.00401\ x}$ | 0.972 | | 401 |
| | C (Ethane/Methane) | 3 | $y = 0.0351\ e^{0.00560\ x}$ | 0.781 | | 560 |
| | D (Methane/Hydrogen) | 4 | $y = 0.0941\ e^{0.00792\ x}$ | 0.919 | | 792 |
| | E (Ethane/Hydrogen) | 5 | $y = 0.00330\ e^{0.0135\ x}$ | 0.866 | | 1350 |
| | F (Ethylene/Hydrogen) | 6 | $y = 0.0257\ e^{0.0119\ x}$ | 0.943 | | 1190 |
| Natural Ester Oil | A (Ethylene/Ethane) | 21 | $y = 1.67\ e^{0.000688\ x}$ | 0.075 | 0.758 | 69 |
| | B (Ethylene/Methane) | 22 | $y = 0.0152\ e^{0.00891\ x}$ | 0.902 | | 891 |
| | C (Ethane/Methane) | 23 | $y = 0.0192\ e^{0.00698\ x}$ | 0.787 | | 698 |
| | D (Methane/Hydrogen) | 24 | $y = 0.102\ e^{0.00720\ x}$ | 0.936 | | 720 |
| | E (Ethane/Hydrogen) | 25 | $y = 0.00195\ e^{0.0142\ x}$ | 0.919 | | 1420 |
| | F (Ethylene/Hydrogen) | 26 | $y = 0.00429\ e^{0.0144\ x}$ | 0.930 | | 1440 |

TABLE 6

Range of Heating Temperatures: 100° C. to 900° C.

| Type of Oil | Concentration Ratio Between Gas Components | FIG. | Approximation Expression | Coefficient of Correlation | | k × 100000 |
|---|---|---|---|---|---|---|
| Synthetic Ester Oil | G (Acetylene/Hydrogen) | 17 | $y = 0.00000465\ e^{0.0149\ x}$ | 0.969 | 0.990 | 1490 |
| | H (Acetylene/Methane) | 18 | $y = 0.000000330\ e^{0.0146\ x}$ | 0.994 | | 1460 |
| | I (Acetylene/Ethane) | 19 | $y = 0.0000000801\ e^{0.0164\ x}$ | 0.999 | | 1640 |
| | J (Acetylene/Ethylene) | 20 | $y = 0.000000205\ e^{0.0133\ x}$ | 0.998 | | 1330 |
| Natural Ester Oil | G (Acetylene/Hydrogen) | 37 | $y = 0.000583\ e^{0.00784\ x}$ | 0.979 | 0.993 | 784 |
| | H (Acetylene/Methane) | 38 | $y = 0.0000669\ e^{0.00768\ x}$ | 1.000 | | 768 |
| | I (Acetylene/Ethane) | 39 | $y = 0.00000874\ e^{0.00989\ x}$ | 0.997 | | 989 |
| | J (Acetylene/Ethylene) | 40 | $y = 0.0000132\ e^{0.00765\ x}$ | 0.995 | | 765 |

TABLE 7

| Categorization | | Concentration Ratio Between Gas Components Appropriate as Indicator |
|---|---|---|
| Heating Temperature | Acetylene | Possibility of Stray Gassing | for Estimation of Overheating Temperature |
| 100° C. to 700° C. | No | No | E (Ethane/Hydrogen) F (Ethylene/Hydrogen) |
| | | Yes | B (Ethylene/Methane) C (Ethane/Methane) |
| 100° C. to 900° C. | Yes | No | G (Acetylene/Hydrogen) I (Acetylene/Ethane) |
| | | Yes | H (Acetylene/Methane) I (Acetylene/Ethane) |

(Preparation of Overheating Temperature Evaluation Diagram)

Since the concentration ratios shown in Table 7 highly correlate with a heating temperature of insulating oil and is great in variation with variation in temperature (high in inclination of the graph), they can serve as suitable indicators for estimation of an overheating temperature of an oil-immersed electric appliance.

FIGS. 41 to 44 each show an overheating temperature evaluation diagram prepared for synthetic ester oil based on the concentration ratio between gas components appropriate as the indicator for estimation of an overheating temperature in four cases shown in Table 7. Similarly, FIGS. 45 to 48 each show an overheating temperature evaluation diagram prepared for natural ester oil based on the concentration ratio between gas components appropriate as the indicator for estimation of an overheating temperature in four cases shown in Table 7.

In FIGS. 41 to 48, a region I (A) is a region corresponding to a concentration ratio between gas components generated when a temperature of ester oil is not higher than 300° C. A region II (B to D) is a region corresponding to a concentration ratio between gas components generated when a temperature of ester oil exceeds 300° C. and is not higher than 700° C. In FIGS. 43, 44, 47, and 48, a region III (E to G) is a region corresponding to a concentration ratio between gas components generated when a temperature of ester oil exceeds 700° C. and is not higher than 900° C.

When a concentration ratio between gas components is in "region D" in region II in FIGS. 41 to 48, it can be estimated that overheat abnormality exceeding 300° C. and not higher than 700° C. has occurred. Determination as occurrence of overheat abnormality exceeding 300° C. and not higher than 700° C. more reliable than determination as occurrence of a fault in region II (any of regions B to D) can thus be made.

Similarly, when a concentration ratio between gas components is in "region G" in region III in FIGS. 43, 44, 47, and 48, it can be estimated that overheat abnormality exceeding 700° C. and not higher than 900° C. has occurred. Determination as occurrence of overheat abnormality exceeding 700° C. and not higher than 900° C. more reliable than determination as occurrence of a fault in region III (any of regions E to G) can thus be made.

Areas of regions A, D, and G reflect inclinations of the approximation expressions in Table 2, and as the combination is higher in inclination, the area of each region is larger. Evaluation of an overheating temperature can thus be considered as being highly accurate.

In estimating an overheating temperature, an appropriate overheating temperature evaluation diagram is desirably selected from among the overheating temperature evaluation diagrams shown in FIGS. 41 to 48 in accordance with a result of analysis of gas components actually contained in ester oil in an oil-immersed electric appliance (see the second embodiment and FIG. 49).

It should be understood that the embodiments and the examples disclosed herein are illustrative and non-restrictive in every respect. The scope of the present invention is defined by the terms of the claims rather than the description above and is intended to include any modifications within the scope and meaning equivalent to the terms of the claims.

REFERENCE SIGNS LIST 1 ester oil; 21 test vessel; 22 conservator; 31 heater; 32 AC power supply; 41, 42 thermometer; 5 agitator; and 6 oil taking syringe

The invention claimed is:

1. A method of estimating an overheating temperature of an oil-immersed electric appliance in which ester oil is used as insulating oil, the method comprising:
   extracting sample gas from the ester oil, wherein the sample gas is dissolved in the ester oil;
   measuring, by a gas separation device, a plurality of gas components in the extracted sample gas;
   estimating, from the extracted sample gas, the overheating temperature based on a first concentration ratio representing a concentration ratio between two types of gas components contained in the ester oil and a second concentration ratio representing a concentration ratio between two types of gas components, at least one of which is different from the two types of gas components in the first concentration ratio, contained in the ester oil; and
   determining whether to perform a safety measure responsive to an occurrence of an overheat abnormality based on the estimated overheating temperature,
   when the ester oil contains acetylene, either the first concentration ratio or the second concentration ratio is a concentration ratio between acetylene and ethane, and
   when the ester oil does not contain acetylene, either of the first concentration ratio or the second concentration ratio is a concentration ratio between ethylene and hydrogen or a concentration ratio between ethane and hydrogen.

2. The method according to claim 1, wherein
   when the ester oil contains acetylene, the first concentration ratio and the second concentration ratio respectively are the concentration ratio between acetylene and ethane and the concentration ratio between acetylene and methane, and
   when the ester oil does not contain acetylene, the first concentration ratio and the second concentration ratio respectively are the concentration ratio between ethylene and hydrogen and the concentration ratio between ethane and hydrogen.

3. A method of estimating an overheating temperature of an oil-immersed electric appliance in which ester oil is used as insulating oil, the method comprising:
   extracting sample gas from the ester oil, wherein the sample gas is dissolved in the ester oil;
   measuring, by a gas separation device, a plurality of gas components in the extracted sample gas;
   estimating, from the extracted sample gas, the overheating temperature based on a first concentration ratio representing a concentration ratio between two types of gas components contained in the ester oil and a second concentration ratio representing a concentration ratio between two types of gas components, at least one of which is different from the two types of gas components in the first concentration ratio, contained in the ester oil; and determining whether to perform a safety measure responsive to an occurrence of an overheat abnormality based on the estimated overheating temperature, wherein when the ester oil contains acetylene, the first concentration ratio and the second concentration ratio are selected from:
  a concentration ratio of acetylene to ethane,
  a concentration ratio of acetylene to hydrogen,
  a concentration ratio of acetylene to methane, and
  a concentration ratio of acetylene to ethylene, and when the ester oil does not contain acetylene, the first concentration ratio and the second concentration ratio are selected from:
  a concentration ratio of ethylene to hydrogen,
  a concentration ratio of ethane to hydrogen,
  a concentration ratio of ethylene to methane, and
  a concentration ratio of methane to ethane.

4. The method according to claim 1, wherein the overheating temperature is estimated by division into areas of an overheating temperature evaluation diagram in which a horizontal axis represents the first concentration ratio and a vertical axis represents the second concentration ratio and by determination as to in which area in the overheating temperature evaluation diagram a plot corresponding to measurement values of the first concentration ratio and the second concentration ratio is located.

* * * * *